(12) United States Patent
Evans et al.

(10) Patent No.: US 6,673,587 B1
(45) Date of Patent: Jan. 6, 2004

(54) HISTONE DEACETYLASE, AND USES THEREFOR

(75) Inventors: Ronald M. Evans, La Jolla, CA (US); Hung-Ying Kao, San Diego, CA (US); Michael Downes, San Diego, CA (US); Peter Ordentlich, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 38 days.

(21) Appl. No.: 09/637,145

(22) Filed: Aug. 11, 2000

(51) Int. Cl.$^7$ .............................. C12N 9/16; C12N 1/20; C12N 15/00; C07H 21/04; C07K 1/00
(52) U.S. Cl. .......................... 435/196; 435/6; 435/7.1; 435/252.3; 435/320.1; 536/23.2; 530/350
(58) Field of Search .............................. 435/196, 252.3, 435/320.1, 6, 7.1; 536/23.2; 530/350, 300

(56) References Cited

PUBLICATIONS

Sequence search alignment between SEQ ID NO : 1 and AF239243.*
Alland et al., Role for N–CoR and histone deacetylase in Sin3–mediated transcriptional repression, Nature, 1997, 387:49–55.
Archer et al., "Histone acetylation and cancer," Current Opin. Genet. Dev., 1999, 9:171–174.
Asahara et al., Pbx–Hox heterodimers recruit coativator- -corepressor complexes in an isoform–specific manner, Mol. Cell. Biol., 1999, 19:8219–8225.
Bailey et al., "The Nuclear receptor corepressor N–CoR regulates differentiation: N–CoR directly interacts with MyoD," Mol. Endo., 1999, 13:1155–68.
Bannister et al., "The CBP co–activator is a histone acetyltransferase," Nature, 1996, 384:641–643.
Blanco et al., "The histone acetylase PCAF is a nuclear receptor coactivator," Genes & Development 1998, 12:1638–51.
Carmen et al., "HDA1 and HDA3 are components of a yeast deacetylase (HAD) complex," J. Biol. Chem., 1996, 271:15837–44.
Chen et al., "Nuclear receptor coactivator ACTR is a novel histone acetyltransferase and forms a multimetric activation complex with P/CAF and CBP/p300," Cell, 1997, 90:569–80.
Chen et al., "A transcriptional co–repressor that interacts with nuclear hormone receptors," Nature, 1995, 377:454–57.
Cress et al., "Histone deacetylases, transcriptional control, and cancer," Journal of Cellular Phy., 2000, 184:1–16.
Dhordain et al., "Corepressor SMRT binds the BTB/POZ repressing domain of the LAZ3/BCL6 oncoprotein," Proc. Nat. Acad. Sci. USA, 1997, 94:10762–67.

Doetzlhofer et al., "Histone deacetylase 1 can repress transcription by binding to Sp1," Mol. And Cell. Biol., 1999, 19:5504–11.
Dressel et al., "Alien, a highly conserved protein with characteristics of a compressor for members of the nuclear hormone receptor superfamily," Mol. and Cell. Biol., 1999, 19:3383–94.
Emillani et al., "Characterization of a human RPD3 ortholog, HDAC3," Proc. Nat. Acad. Sci. USA, 1998, 95:2795–2800.
Fenrick et al., "Role of histone deacetylases in acute leukemia," J. Cell. Biochem. Supp., 1998, 30:194–202.
Fischle et al., "A New Family of human histone deacetylases related to *Saccharomyces cerevisiae* HDA1p," J. of Biolog. Chem., 1999, 274:11713–20.
Grozinger et al., "Three proteins define a class of human histone deacetylases related to yeast HDA1p," Proc. Nat. Acad. Sci. USA, 1999, 96:4868–4873.
Hassig et al., "Histone deacetylase activity is required for full transcriptional repression by mSin3A," Cell, 1987, 89:341–47.
He et al., "Distinct interactions of PML–RAR= and PLZ-F–RARα with co–repressors determine differential responses to RA in APL," Nature Genetics, 1998, 18:126–135.
Heinzel et al., "A complex containing N–CoR, mSin3 and histone deacetylase mediates transcriptional repression," Nature, 1997, 387:43–48.
Hong et al., "GRIP1, a novel mouse protein that serves as a transcriptional coactivator in yeast for the hormone binding domains of steroid receptors," Proc. Nat. Acad. Sci. USA, 1996, 93:4948–52.

(List continued on next page.)

*Primary Examiner*—Tekchand Saidha
(74) *Attorney, Agent, or Firm*—Stephen E. Reiter; Foley & Lardner

(57) ABSTRACT

The present invention relates to the identification, isolation, sequencing and characterization of a new member of the histone deacetylase family, as well as its transcripts, gene products, associated sequence information, and related genes. The present invention also relates to methods for detecting and diagnosing carriers of normal and mutant alleles of these genes, methods for detecting and diagnosing diseases, methods of identifying genes and proteins related to or interacting with such genes and proteins, methods of screening for potential therapeutics for diseases, methods of treatment for diseases, and to cell lines and animal models useful in screening for and evaluating potentially useful therapies for diseases. In a particular aspect of the present invention, a novel family member, HDAC7, is described and its interaction with SMRT/N-CoR and mSin3A, its biochemical properties and subcellular localization are characterized. In addition, evidence is provided that the HDAC4, 5, and 7 deacetylases may mediate nuclear receptor repression. The findings described here indicate that two or more classes of histone deacetylases can collectively contribute to SMRT/N-CoR action and that at least some deacetylases may directly associate with SMRT/N-CoR in a mSin3A independent fashion.

25 Claims, 9 Drawing Sheets

OTHER PUBLICATIONS

Hong et al., "SMRT corepressor interacts with PLZF and with the PMNL–retinoic acid receptor α (RARα) and PLZ-F–RARα oncoproteins associated with acute promyelocytic leukemia," Proc. Nat. Acad. Sci. USA, 1997, 94:9028–33.

Horlein et al., "Ligand–independent repression by the thyroid hormone receptor mediated by a nuclear receptor co–repressor," Nature, 1995, 377:397–403.

Huynh et al., "The BCL–6 POZ domain and other POZ domains interact with the co–repressors N–CoR and SMRT," Oncogene, 1998, 17:2473–84.

Iavarone et al., "E2F and histone deacetylase mediate transforming growth factor β repression of cdc25A during keratinocyte cell cycle arrest," Mol. and Cell. Biol., 1999, 19:916–922.

Kamei et al., "A CBP integrator complex mediates transcriptional activation and AP–1 inhibition by nuclear receptors," Cell, 1996, 85:403–414.

Kao et al., "A histone deacetylase corepressor complex regulates the Notch signal transduction pathway," Genes & Development, 1998, 12:2269–77.

Khochbin et al., "Hypothesis: The origin and utility of histone deacetylases," FEBS Letters, 1997, 419:157–160.

Kraus et al., "Detection and isolation of novel protein–tyrosine kinase genes employing reduced stringency hybridization," Methods in Enzymology, 1991, 200:546–556.

Laherty et al., "Histone deacetylases associated with the mSin3 corepressor mediate mad transcriptional repression," Cell, 1997, 89:349–5.

Lin et al., "Role of the histone deacetylase complex in acute promyelocytic leukaemia," Nature, 1998, 391:811–14.

Mangelsdorf et al., "The nuclear receptor superfamily: the second decade," Cell, 1995, 83:835–839.

Mangelsdorf et al., "The RXR heterodimers and orphan receptors," Cell, 1995, 83:841–850.

Miska et al., "HDAC4 deacetylase associates with and represses the MEF2 transcription factor," The EMBO Journal, 1999, 18:5099–5107.

Muto, et al., "Identification of Bach2 as a B–cell–specific partner for small Maf proteins that negatively regulate the immunoglobulin heavy chain gene 3' enhancer," EMBO Journal, 1998, 17:5734–43.

Nagy et al., "Nuclear receptor repression mediated by a complex containing SMRT, mSin3A, and histone deacetylase," Cell, 1997, 89:373–380.

Needleman et al., "A general method applicable to the search for similarities in the amino acid sequence of two proteins," J. Mol. Biol., 1970, 48:43–453.

Ogryzko et al., "The transcriptional coactivators p300 and CBP are histone acetyltransferases," Cell, 1996, 87:953–959.

Onate et al., "Sequence and characterization of a coactivator for the steroid hormone receptor superfamily," Science, 1995, 270:1354–1357.

Ordentlich et al., "Unique forms of human and mouse nuclear receptor corepressor SMRT," Proc. Nat. Acad. Sci. USA, 1999, 96:2639–44.

Pearson et al., "Improved tools for biological sequence comparison," Proc. Nat. Acad. Sci. USA, 1988, 85:2444–2448.

Radkov et al., "Epstein–Barr virus nuclear antigen 3C interacts with histone deacetylase to repress transcription," 1999, 73:5688–97.

Rundlett et al., "HDA1 and RPD3 are members of distinct yeast histone deacetylase complexes that regulate silencing and transcription," Proc. Nat. Acad. Sci. USA, 1996, 93:14503–08.

Smith et al., "Comparison of Biosequences," Advances in Applied Mathematics, 1981, 2:482–489.

Spencer et al., "Steroid receptor coactivator–1 is a histone acetyltransferase," Nature, 1997, 389:194–198.

Torchia et al., "The transcriptional co–activator p/CIP binds CBP and mediates nuclear–receptor function," Nature, 1997, 387:677–84.

Verdel et al., "Identification of a new family of higher eukaryotic histone deacetylases," Journal of Biological Chemistry, 1999, 274:2440–2445.

Wong et al., "Components of the SMRT corepressor complex exhibit distinctive interactions with the POZ domain oncoproteins PLZF, PLZF–RARα and BCL–6," Journal of Biological Chemistry, 1998, 273:27695–702.

Yang et al., "A p300/CBP–associated factor that competes with the adenoviral oncoprotein E1A," Nature, 382:319–324.

Yao et al., "The nuclear hormone receptor coactivator SRC–1 is a specific target of p3000," Proc. Nat. Acad. Sci. USA, 1996, 93:10626–31.

Yoshida et al., "Trichostatin and Leptomycin: Inhibition of histone deacetylation and signal–dependent nuclear export," Ann. NY Acad. Sci., 1999, 886:23–36.

Zamir et al., "A Nuclear hormone receptor corepressor mediates transcriptional silencing by receptors with distinct repression domains," Mol. Cell. Biol., 1996, 16:5458–65.

Zhang et al., "Histone deacetylases and SAP18, a novel polypeptide, are components of a human Sin3 complex," Cell, 1997, 89:357–364.

Zwiebel, "New agents for acute myelogenous leukemia," Leukemia, 2000, 14:488–490.

* cited by examiner

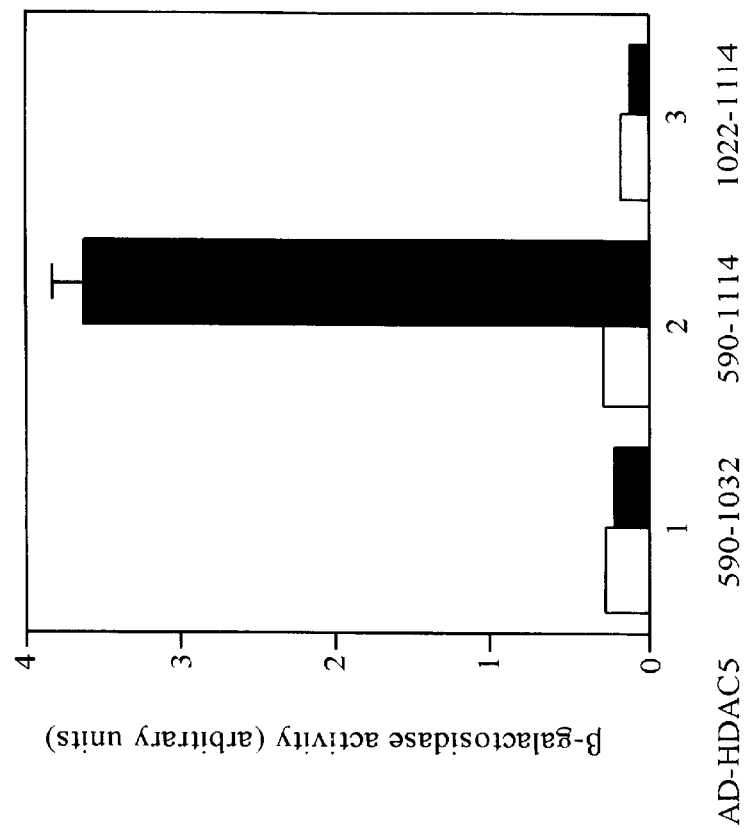
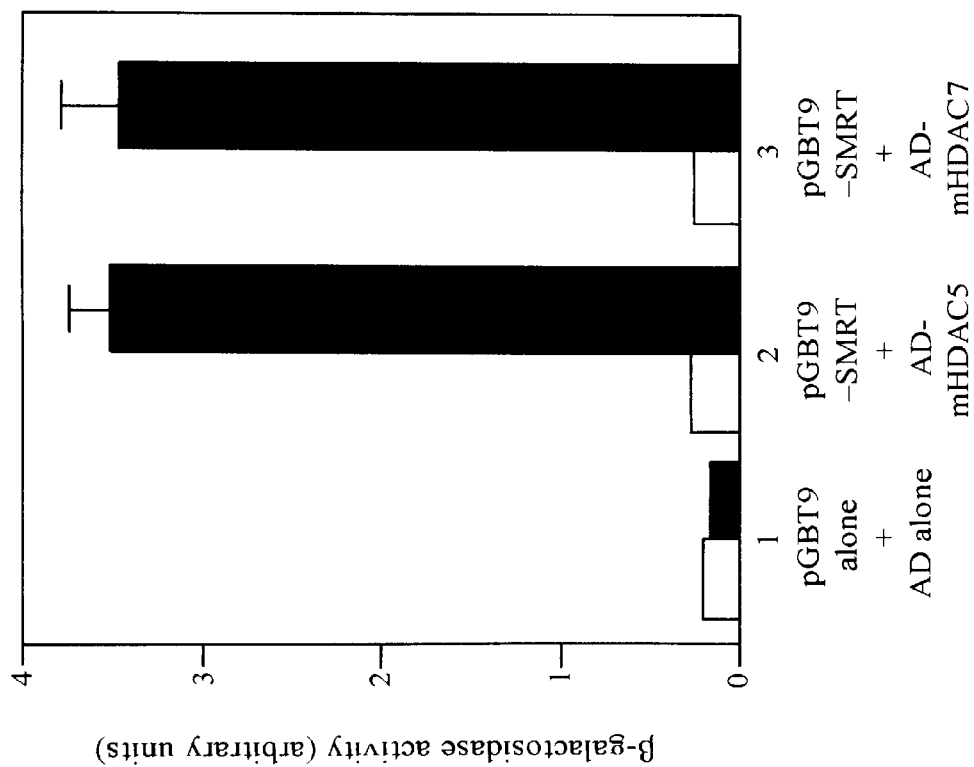
FIG. 1A
FIG. 1B

|  |  | SEQ ID NO:3 |
|  |  | SEQ ID NO:4 |
|  |  | SEQ ID NO:2 |

```
  1  MSS-QSHPDGLSGRDQPVELLNEARVNHMPSTVDVATALPLQVAPS----------AVPMDLRLDHQFSLPV   hHDAC4
  1  MNSPNESADGMSGREPSLEILPRTPLHSIPVAVEVKPVLEGAMPSSMGGGGGSPSPVELRG-----ALAG    mHDAC5
  1  MHSPGAGCPAL-------------QPDTPGSQPQPMDLRVGQRPTVEPP-----------PEPA-         mHDAC7

62  A-EPALREQQLQQELLALKQKQQIQRQILIAEFQRQHEQLSRQHEAQLHEHIKQQQEMLAMKHQQELLEH    hHDAC4
 67  PMDPALREQQLQQELLVLKQQQLQQQLQLLIAEFQKQHDHLTRQHEVQLQKHLKQQQEMLAAKRQQEL-EQ   mHDAC5
 41  ------------LLILQHPQRLRLHRLFLA------------------------GLHQQRS-AE-         mHDAC7

131  QRKLERHRQEQELEKQHREQKLQQLLNKEKGKESAVASTEVKMKLQEFMLNKKKALAHRNINHCISSDPR    hHDAC4
136  QRQREQRQE-ELEKQRLEQQLLILRNKEKSKESAIASTEVKLRLQEFLLSKSKEPTPGGLNHSLPQHPK     mHDAC5
 68  PMRLSMDPPMPELQGGQEQELRQLINKDKSKRSAVASSVVKQKLAEVILKKQQAALERTVHPSSPSIP-     mHDAC7

201  YMVGKTQHSLD--QSSPPQSG----VSTSYNHPVLG-MYDAKDDFPLRKTASEPNLKLRSRLKQKVAERR    hHDAC4
205  CW---GAHHASLD-QSSPPQSGPPGTPPSYKLPLLG-PYDSRDFPLRKTASEPNLKVRSRLKQKVAERR     mHDAC5
137  ------YRTLEPLDTEGAARS---VLSSFLPPVPSLPTEPPEHFPLRKTVSEPNLKLRYKPKKSL-ERR     mHDAC7

265  SSPLLRRKDGPVVTALKKRPLDVTDSA------CSSAPGSGPSSPNSSGSVSAENGIAPAVPSIPAETS    hHDAC4
270  SSPLLRRKDGTVISTFKKRAVEITGPGVSSVQNSAPGSGPSSPNSSHSTI-AENGFTGSVPNLPTEMI     mHDAC5
196  KNPLLRKESAP--PSLRRRPAETLG------DSPSPSSTPASGCSSPNDSEHGPNPALGSEADGDR      mHDAC7

329  LAHRLVAREGSAAPLPLYTSPSLPNITLGLPATGPSAGT---------AGQQDTERLTIPALQQRLSLFPG   hHDAC4
339  PQHRALPLDSSPNQFSLYTSPSLPNISLGLQATVTVNSHLTASPKLSTQQEAERQALQSLRQ----GG      mHDAC5
255  RTHSTLG--------PRGPVLQN-----------PH--                                    mHDAC7

391  THLTEVLSTS---------PLERDGGA-AHSPLLQHM---VLLEQPPAQAPL---VTLGLGALPLHAQS-LV hHDAC4
404  TLTGKFMSTSSIPGCLLGVALEGDTSPHGHASLLQHVCSWT----GRQQSTL-I---AVPLHGQSPLV      mHDAC5
272  ---ABLFLHH------PSLRQPI----LLIDPSVSHAPLWT-VPGLGPLPFHFAQPLL                mHDAC7

445  GADRVSPSIH---KLRQHRPLGRTQSAPLPQNAQALQHVIQQQHQQFLEKHKQQ-FQQQQLQMNKTIIPKP   hHDAC4
464  TGERVATSMRTVGKLPRHRPLSRTQSSPLPQSEPALQQLVMQQHQQQFLEKQKQQ--QMQLGKITTKT      mHDAC5
326  -----ITERLSGS----------GLHRPLNRTRSEPLEPSATAPLLAPLQPRQDRLKPHVQ----LIKP     mHDAC7

512  SEPARQPESHPEETEEELREH--QALLDEPYLD---RLPGQKEAHAQAGVQVKQEPIESDEEEAEPPREVEP hHDAC4
530  GELSRQPTTHPEETEEELREH-IEQEALLQGEALTIPREGSTESESTQEDLEEEEEEEEEEDCIQVKD-ED   mHDAC5
377  AISPPQRPAKPSEK------------------PRLRQIPSAEDLETDGGVGPMANDGLEHRESGR         mHDAC7
```

FIG. 2A-1

```
                                                                                                                              hHDAC4
579   GQRQPSEQELLFRQA-------LLL-EQQRIHQLRNYQASMEAAGIPVSFGGHRPLSRAQSSPASATFPVSV                                                  hHDAC4
599   GESGPDEGPDLEESSAGYKKLFA-DAQQLPLQVYQAPLSLATVP---HQALGRTQSSPAA----PGSM                                                     mHDAC5
425   GPPEGRGSISLQQHQQ-----VPPWEQQHLAGRLSQGSEGDSVLLPLAQVGHRPLSRTQSSPAA----PVSM                                                 mHDAC7

644   QEP--------PTKPR------FTTGLVYDTLMLKHQCTCGSSSHPEHAGRIQSIWSRLQETGLRGKCE                                                    hHDAC4
660   KSP--------TDQPTVVKHLFTTQMVYDTFMLKHQCMCGNTHVHPEHAGRIQSIWSRLQETGLLGKCE                                                    mHDAC5
488   LSPEPTCQTQVLNSSEH------PATGLVYDSVMLKHQCSCGDNSKHPEHAGRIQSIWSRLQERGLRSQCE                                                  mHDAC7

700   CIRGRKATLEELQTVHSEAHTLLYGTNPLNRQKLDSKKLLGSLA--SVFVRLPCGGVGVDSDTIWNEVHSA                                                   hHDAC4
721   RIRGRKATLDEIQTVHSEYHTLLYGTNPLNRQKLDSKKLLGPISQKMYAMLPCGGYGVDSDTIWNEMHSS                                                    mHDAC5
553   CIRGRKASLEELQSVHSERIVLLYGTNPLSRLKLDNGKLTGLLAQRTFVMLPCGGVGVDTDTIWNELHSS                                                    mHDAC7

769   GAARLAVGCVVELVFKVATGELKNGFAVVRPPGHHAEESTPMGFCYFNSVAVAAKLLQQRLSVSKILIVD                                                    hHDAC4
791   SAVRMAVGCIVELAFKVAAGELKNGFAVVRPPGHHAEESTAMGFCFFNSVAITAKLLQQKLSVGKVLIVD                                                    mHDAC5
623   NAARMAAGSVTDLAFKVASRELKNGFAVVRPPGHHADHSTAMGFCFFNSVAIACRQLQQHGKASKILIVD                                                    mHDAC7

839   WDVHHGNGTQAFYSDPSVLYMSLHRYDDGNFFPGSGAPDEVGTGPGVGFNVNMAFTGGLDPPMGDAEYL                                                     hHDAC4
861   WDIHHGNGTQAFYNDPSVLYISLHRYDNGNFFPGSGAPEEVGGGPGVGYNVNVAWTGGVDPPHGDMEYL                                                     mHDAC5
693   WDVHHGNGTQQTFYQDPSVLYISLHRFDDGNFFPGSGAVDEVGTASGEGFNVNVAWAGLDPPMGDPEYL                                                     mHDAC7

909   AAFRTVVMPIASEFAPDVVLVSSGFDAVEGHPTPLGGYNLSARCFGYLTKQLMGLAGGRIVLALEGGHDL                                                    hHDAC4
931   TAFRTVVMPIAQEFSPDVVLVSAGFDAVEGHLSPLGGYISVTARCFGHLTRQLMTLAGGRVVLALEGGHDL                                                   mHDAC5
763   AAFRIVVMPIAREFAPDIVLVSAGFDAAEGHPAPLGGYHVSAKCFGYMTQQLMNLAGAVVLALEGGHDL                                                     mHDAC7

979   TAICDASEACVSALLGNELDPLPEKVLQQRPNANAVRSMEKVMEIHSKYWRCLQRTTSTAGRSLIEAQTC                                                    hHDAC4
1001  TAICDASEACVSALLSVELQPLDEAVLQQKPSVNAVATLEKVIEIQSKHWSCVQRFAAGLGCSLREAQTG                                                    mHDAC5
833   TAICDASEACVAALLGNKVDPLSEESWKQKPNLSATRSLEAVVRVHRKYWGCMQRLASCPDSWLPRV-PG                                                    mHDAC7

1049  ENEEAETVTAMASLSVGVKPAEK---------RPDEEPMEEEPP--L                                                                           hHDAC4
1071  EKEEAETVSAMALLSVGAEQAQAVATQEHSPRPAEEPMEQEPA--L                                                                            mHDAC5
902   ADAEMEAVTATASLSVGI-LAED---------RPSERLVEEEPMNL                                                                            mHDAC7
```

HISTONE DEACETYLASE, AND USES THEREFOR

ACKNOWLEDGMENT

This invention was made with United States Government support under Grant Nos. HD-27183 and DK-57978, awarded by the National Institutes of Health. The Government has certain rights in the invention.

FIELD OF THE INVENTION

The present invention relates to the identification, isolation, sequencing and characterization of a new member of the histone deacetylase family, as well as its transcripts, gene products, associated sequence information, and related genes. The present invention also relates to methods for detecting and diagnosing carriers of normal and mutant alleles of these genes, methods for detecting and diagnosing diseases, methods of identifying genes and proteins related to or interacting with such genes and proteins, methods of screening for potential therapeutics for diseases, methods of treatment for diseases, and cell lines and animal models useful in screening for and evaluating potentially useful therapies for diseases. In a particular aspect of the present invention, a novel family member, HDAC7, is described, and its interaction with SMRT/N-CoR and mSin3A, its biochemical properties and subcellular localization are all characterized. In addition, evidence is provided that the HDAC4, 5, and 7 deacetylases mediate nuclear receptor repression. The findings described here indicate that two or more classes of hi stone deacetylases can collectively contribute to SMRT/N-CoR action and that at least some deacetylases may directly associate with SMRT/N-CoR in an mSin3A independent fashion.

BACKGROUND OF THE INVENTION

Nuclear hormone receptors are sequence-specific and ligand-dependent transcription factors that control cell proliferation, differentiation, and animal physiology (Mangelsdorf and Evans, (1995) Cell, 83:841–850; Mangelsdorf et al., (1995) Cell, 83:835–839). They are structurally related and contain two evolutionarily conserved modules, the DNA binding (DBD) and ligand-binding domains (LBD). Several receptors including retinoic acid and thyroid hormone receptors function as potent repressors in the absence of ligands and as activators upon ligand binding. Intensive studies on the mechanism of transcriptional activation by nuclear hormone receptors led to the identification of coactivators including CBP/p300, PCAF, as well as the p160 family proteins (SRC-1; GRIP1/TIF2; ACTR/RAC3/P/CIP) (Blanco et al., (1998) Genes & Devel., 12:1638–51; Chen et al., (1997) Cell, 90:569–80; Hong et al., (1996) Proc. Natl. Acad. Sci. USA, 93:4948–52; Kamei et al., (996) Cell, 85: 403–414; Onate et al., (1995) Science, 270:1354–57; Torchia et al., (1997) Nature, 387:677–84; Yao et al., (1996) Proc. Nati. Acad. Sci. USA, 93:10626–31). Among these, CBP, PCAF, and SRC-1/ACTR have been recently shown to possess intrinsic histone acetyltransferase activity, consistent with a role for histone acetylation in transcriptional activation (Bannister and Kouzarides, (1996) Nature, 384:641–43; Chen et al., (1997) Cell, 90:569–80; Ogryzko et al., (1996) Cell, 87:953–59; Spencer et al., (1997) Nature, 389:194–98; Yang et al., (1996) Nature, 382:12845–50).

Several corepressors for nuclear receptors including SMRT, N-CoR, SUN-CoR, and Alien have also been identified (Chen and Evans, (1995) Nature, 377:454–57; Dressel et al., (1999) Cell. Blo., 19:3383–94; Horlein et al., (1995) Nature, 377:397–404; Ordentlich et al., (1999) Proc. Natl. Acad. Sci. USA, 96:2639–44; Zamir et al., (1996) Mol. Cell. Biol., 16:5458–65). SMRT and N-CoR were identified by yeast two-hybrid screens with nuclear receptors. Both proteins are large and possess at least four autonomous repression domains.

In addition to nuclear receptors, functional associations between SMRT/N-CoR with other transcription factors including CBF1/RBPJK, PLZF, BCL6, MyoD, Bach2, and Pbx1 have been demonstrated (Asahara et al., (1999) Mol. Cell. Biol., in press; Bailey et al., (1999) Mol. Endocrinol., 13:1155–68; Dhordain et al., (1997) Proc. Natl. Acad. Sci. USA, 94:10762–67; He et al., (1998) Nat Genet 18:126–35; Hong et al., (1997) Proc. Natl. Acad. Sci. USA, 94:9028–33; Huynh and Bardwell, (1998) Oncogene, 17:2473–84; Kao et al., (1998) Genes & Devel. 12:2269–77; Lin et al., (1998) Nature, 391:811–14; Muto et al., (1998) EMBO J., 17:5734–43; Wong and Privalsky, (1998) J. Biol. Chem., 273:27695–702), suggesting that corepressors, like coactivators, may function as signaling integrators to control cell fate. Several lines of evidence suggest that the mechanism underlying the repressive activity of SMRT and N-CoR corepressors is manifested through their recruitment of a histone deacetylase complex containing mSin3A and HDAC1 (Alland et al., (1997) Nature, 387:49–55; Hassig et al., (1997) Cell, 89:341–47; Heinzel et al., (1997) Nature, 387:43–48; Laherty et al., (1997) Cell, 89–349–56; Nagy et al., (1997) Cell, 89:373–80; Zhang et al., (1997) Cell, 357–64). Recruitment of acetylase/deacetylase complexes by coactivators/corepressors is thought to cause a local change in the chromatin structure, resulting in either activation or repression of gene transcription.

In yeast Sacchromyces cerevisiae, two distinct histone deacetylase complexes have been characterized (Carmen et al., (1996) J. Biol. Chem., 271:15837–44; Rundlett et al., (1996) Proc. Natl. Acad. Sci. USA, 93:14503–08). Histone deacetylase-B (HDB) is a 600 kDa complex which contains the Rpd3 protein. Histone deacetylase-A (HDA) is a 350 kDa complex and contains yeast Hda1 and the related Hos1, 2, and 3. Homology studies indicate that the HDA1-related deacetylases are structurally distinct from Rpd3 (which appears to be most related to mammalian class I deacetylases HDAC1, 2, and 3). Class II mammalian histone deacetylases (HDAC4, 5, and 6) have been recently identified which are structurally related to yeast Hda1 (Fischle et al., (1999) J. Biol. Chem., 274:11713–20; Grozinger et al., (1999) Proc. Natl, Acad. Sci. USA, 96:4868–73; Verdel and Khochbin, (1999) J. Biol. Chem., 2440–45). These family members are large in size (from 1085 amino acids to 1216 amino acids) and are able to deacetylate histones in vitro. HDAC4 and HDAC5 (also known as mHDA1) are highly homologous (51%/63% in identity/homology) and contain a conserved C-terminal deacetylase domain (89% amino acid identity). Intriguingly, HDAC6 (also known as mHDA2) has two catalytic domains at the amino-terminal, which have been suggested to form an intramolecular dimer. While HDAC4 has been shown to coprecipitate with HDAC3 and RbAp48, HDAC5 appears to associate with at least HDAC3 (Grozinger et al., 1999, supra). Furthermore, Northern blot analyses indicate that the tissue distribution patterns of family members are quite distinct. Numerous studies have indicated that the HDAC1/HDAC2 complexes are recruited to promoters by sequence-specific DNA-binding transcription factors (Doetzlhofer et al., (1999) Mol. Cell. Biol., 19:5504–11; Emiliani et al., (1998) Proc. Natl. Acad. Sci. USA, 95:2795–800; lavarone and Massague, (1999) Mol.

Cell. Biol., 19:916–22; Radkov et al., (1999) J. Virol., 73:5688–97; Yang et al., (1996)). A recent report suggests that HDAC4 associates with and represses the MEF2 transcription factor (Miska et al., (1999) EMBO J., 18:5099–5107). However, the role of the HDAC4–6 family of histone deacetylases in transcription is largely unknown.

A key event in the regulation of eukaryotic gene expression is the posttranslational modification of nucleosomal histones, which converts regions of chromosomes into transcriptionally active or inactive chromatin. The most well studied posttranslational modification of histones is the acetylation of epsilon-amino groups on conserved lysine residues in the histones' amino-terminal tail domains. Histone acetylation influences both gene transcription and chromatin assembly after DNA replication and the enzymes that regulate this property of chromatin are likely to play a key role in regulating these crucial genomic functions. The steady-state level of histone acetylation is established and maintained by multiple histone acetyltransferases (HATs) and deacetylases (HDACs). Significant advances have been made in the past few years toward the identification of histone acetyltransferases and histone deacetylases.

The HDACs have been implicated in repression of gene expression by facilitating chromatin condensation and, like the HATs, operate as part of multi-protein complexes (Khochbin S, Wolffe AP FEBS Lett (1997) 419(2–3) 157–60). More intriguing, at least some histone deacetylases are associated with chromatin-remodeling machines. The non-catalytic components of these complexes can either target the catalytic subunit to specific sites on the genome or regulate its enzymatic specificity. Kinase and phosphatase activities of intracellular signal transduction pathways may modify components of these complexes and thereby regulate their assembly, targeting or enzymatic function.

Recent efforts to understand the biological role of these enzymes reveals their involvement in cell-cycle regulation and differentiation. In addition, several studies have pointed to the possible involvement of histone deacetylases in human cancer. The availability of cloned histone deacetylase genes provides swift progress in the understanding of the mechanisms of deacetylases, their role in transcription, and their possible role in health and disease (Cress W D, Seto E., J Cell Physiol. 2000 Jul;184(1):1–16).

SUMMARY OF THE INVENTION

The present invention is based, in part, upon the identification, isolation, cloning and sequencing of a novel family member of the histone deacetylase superfamily. By the present invention, a novel family member, HDAC7, is described and its interaction with SMRT/N-CoR and mSin3A, its biochemical properties and subcellular localization are characterized. In addition, evidence is provided that the HDAC4, 5, and 7 deacetylases may mediate nuclear receptor repression.

Thus, in accordance with one embodiment of the present invention, there are provided isolated nucleic acids including nucleotide sequences comprising or derived from the HDAC7 genes and/or encoding polypeptides comprising or derived from the HDAC7 proteins.

In accordance with another embodiment of the present invention, there are provided host cells that have been transfected or otherwise transformed with one or more of invention nucleic acids.

In accordance with still another embodiment of the present invention, there are provided transgenic animal models for neoplasia and other diseases or disorders associated with mutations in HDAC7 genes.

In accordance with a further embodiment of the present invention, there are provided substantially pure protein preparations including polypeptides comprising or derived from HDAC7 proteins.

In accordance with another embodiment of the present invention, there are provided methods for the production and use of polyclonal and monoclonal antibodies, including antibody fragments, including Fab fragments, F(ab')$_2$, and single chain antibody fragments, which selectively bind to HDAC7, or to specific antigenic determinants of HDAC7. The antibodies of the invention may be used in the various diagnostic, therapeutic and technical applications described herein.

In accordance with a still further embodiment of the present invention, there are provided methods of screening or identifying proteins, small molecules or other compounds which are capable of inducing or inhibiting the expression of HDAC7 genes and proteins.

In accordance with yet another embodiment of the present invention, there are provided methods for identifying proteins and other compounds which bind to, or otherwise directly interact with, HDAC7.

In accordance with still another embodiment of the present invention, there are provided methods of identifying proteins, small molecules and other compounds capable of modulating the activity of normal or mutant histone deacetylases, class I and/or class II, preferably HDAC7. In a particular aspect of the present invention, there are provided methods for identifying compounds capable of modulating specifically class I or class II histone deacetylases, more specifically, HDAC7.

In accordance with a further embodiment of the present invention, there are provided methods for screening for carriers of HDAC7 alleles associated with mutations in the HDAC7 genes. Screening and/or diagnosis can be accomplished, for example, by methods based upon the nucleic acids (including genomic and mRNA/cDNA sequences), proteins, and/or antibodies disclosed and enabled herein, including functional assays designed to detect failure or augmentation of the normal HDAC7 activity and/or the presence of specific new activities conferred by the mutant HDAC7s.

In yet another embodiment of the present invention, there are provided methods and pharmaceutical preparations for use in the treatment of histone deacetylase-associated diseases, e.g., HDAC7-associated diseases such as cancers, and the like.

BRIEF DESCRIPTION OF THE DRAWINGS

FIGS. 1A and 1B illustrate the interaction of SMRT repression domains III and IV with deacetylase domain of the newly described deacetylases.

FIG. 1A is a graph quantitation of yeast two-hybrid assays between SMRT and HDAC5 and 7. Yeast cells were co-transformed with the indicated plasmids. Two viable transformants were picked for liquid β-galactosidase activity. The number represents average of duplicates from two colonies.

FIG. 1B is a graph indicating that SMRT interaction requires amino acid C-terminal to the deacetylase domain of mHDAC5. The data was generated employing a yeast two-hybrid assay as described in FIG. 1A.

FIG. 2A is the deduced amino acid sequence of mHDAC7 and sequence alignment of human HDAC4 (SEQ ID NO:3) and mouse HDAC5 (SEQ ID NO:4) and HDAC7 (SEQ ID NO:2). Sequence alignment of HDAC4, 5, and 7 were performed according to the Jotun Hein method using DNA STAR program. The beginning of histone deacetylase domain is indicated as an arrow.

DETAILED DESCRIPTION OF THE INVENTION

Figure 2B:
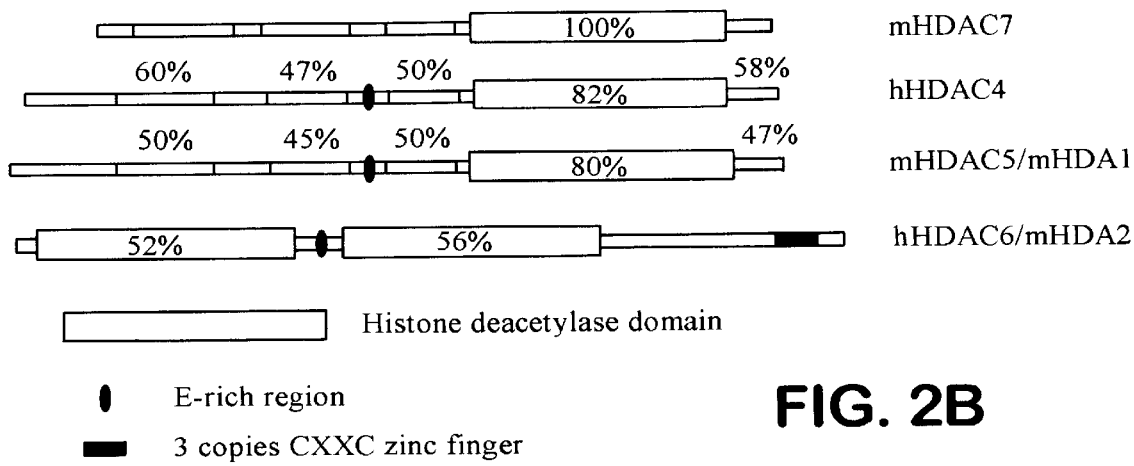
FIG. 2B is a schematic representation of the histone deacetylase family. The percentage of homology in each domain is determined by blasting against the amino acid sequence of mHDAC7. The histone deacetyalse domain is indicated as a blank rectangle. The black dots indicate the position of the glutamate-rich (E-rich) regions. Three copies of the zinc finger motif are shown as black rectangle.

In accordance with the present invention, there are provided isolated polynucleotides encoding a histone deacetylase (HDAC), wherein said histone deacetylase interacts in an mSin3A independent manner with Silencing Mediator for Retinoic acid and Thyroid hormone receptors (SMRT), N-CoR, or an isoform or peptide portion of SMRT or N-CoR, an isolated polynucleotide complementary to said polynucleotide encoding HDAC, and fragments of said polynucleotide encoding HDAC.

In accordance with a further embodiment of the present invention, there are provided isolated nucleic acids corresponding to, or relating to, the HDAC7 nucleic acid sequences disclosed herein. As described more fully below, these sequences include normal and mutant HDAC7 sequences from mammalian species, functional equivalents, homologous sequences from non-mammalian species (e.g., such as Drosophila and C. elegans sequences useful as probes and PCR primers), subsets of these sequences encoding fragments of the proteins or corresponding to particular structural domains or polymorphic regions, complementary or antisense sequences corresponding to above sequences, modifications, derivatives and variants of the above, recombinant polynucleotides comprising sequences encoding functional polypeptides operably joined to exogenous regulatory regions, and sequences encoding fusion proteins of the invention polypeptide fused to other polypeptides (which are useful as markers of expression, as "tags" for purification, or in screens and assays for proteins interacting with HDAC7), and the like.

The HDAC7 sequences of the invention include the specifically disclosed sequences, splice variants of these sequences, allelic variants of these sequences, synonymous sequences, and homologous or orthologous variants of these sequences. Thus, for example, the invention provides genomic and cDNA sequences from the HDAC7 gene. The present invention also provides allelic variants and homologous or orthologous sequences by providing methods by which such variants may be routinely obtained. Because the nucleic acids of the invention may be used in a variety of diagnostic, therapeutic and recombinant applications, various subsets of the HDAC7 sequences and combinations of the HDAC7 sequences with heterologous sequences are also provided. For example, for use in allele specific hybridization screening or PCR amplification techniques, subsets of the HDAC7 sequences, including both sense and antisense sequences, and both normal and mutant sequences, as well as intronic, exonic and untranslated sequences, are provided. Such sequences may comprise a small number of contiguous nucleotides from the sequences which are disclosed or otherwise enabled herein, but preferably include at least 8, and up to about 50 contiguous nucleotides, preferably 9–25, and more preferably 18–24 contiguous nucleotides from an HDAC7 sequence. Other preferred subsets of HDAC7 sequences include those encoding one or more of the functional domains or antigenic determinants of HDAC7 proteins and, in particular, may include either normal (wild-type) or mutant sequences.

The invention also provides for various nucleic acid constructs in which HDAC7 sequences, either complete or subsets, are operably joined to exogenous sequences to form cloning vectors, expression vectors, fusion vectors, transgenic constructs, and the like. Thus, in accordance with another aspect of the invention, a recombinant vector for transforming a mammalian or invertebrate tissue cell to express a normal or mutant HDAC7 sequence in the cells is provided.

As used herein with respect to genes, the term "normal" refers to a gene that encodes a normal protein. As used herein with respect to proteins, the term "normal" means a protein which performs its usual or normal physiological role and which is not associated with, or causative of, a pathogenic condition or state. Therefore, as used herein, the term "normal" is essentially synonymous with the usual meaning of the phrase "wild type." For any given gene, or corresponding protein, a multiplicity of normal allelic variants may exist, none of which is associated with the development of a pathogenic condition or state. Such normal allelic variants include, but are not limited to, variants in which one or more nucleotide substitutions do not result in a change in the encoded amino acid sequence.

As used herein with respect to genes, the term "mutant" refers to a gene which encodes a mutant protein. As used herein with respect to proteins, the term "mutant" means a protein which does not perform its usual or normal physiological role and which is associated with, or causative of, a pathogenic condition or state. Therefore, as used herein, the term "mutant" is essentially synonymous with the terms "dysfunctional," "pathogenic," "disease-causing," and "deleterious." With respect to the HDAC7 genes and proteins of the present invention, the term "mutant" refers to HDAC7 genes/proteins bearing one or more nucleotide/amino acid substitutions, insertions and/or deletions which typically lead to the development of the symptoms of cancer and/or other relevant neoplastic phenotypes (e.g. tumors, metastasis) when expressed in humans. This definition is understood to include the various mutations that naturally exist, including but not limited to those disclosed herein, as well as synthetic or recombinant mutations produced by human intervention. The term "mutant," as applied to the HDAC7 genes, is not intended to embrace sequence variants which, due to the degeneracy of the genetic code, encode proteins identical to the normal sequences disclosed or otherwise enabled herein; nor is it intended to embrace sequence variants which, although they encode different proteins, encode proteins which are functionally equivalent to normal HDAC7 proteins.

In a preferred embodiment of the present invention, isolated nucleic acid sequences are provided which encode normal or mutant versions of HDAC7 proteins. As used herein, an "isolated nucleic acid" is a ribonucleic acid (RNA), deoxyribonucleic acid (DNA), or nucleic acid analog comprising a polynucleotide sequence that has been isolated or separated from sequences that are immediately contiguous (one on the 5' end and one on the 3' end) in the naturally occurring genome of the organism from which it is derived. The term therefore includes, for example, a recombinant nucleic acid which is incorporated into a vector, into an autonomously replicating plasmid or virus, or into the genomic DNA of a prokaryote or eukaryote; or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequences and/or including exogenous regulatory elements, recombinant genes or "minigenes" in which all or some of the introns have been removed, or in which various combinations of the introns and exons and local cis acting regulatory elements have been engineered in propagation or expression constructs or vectors. Examples of such nucleic acid sequences are disclosed herein (e.g., SEQ ID NO:1, corresponding to mouse HDAC7 mRNA). Such constructs may be particularly useful, as described below, in identifying compounds which can induce or repress the expression of HDAC7.

DNA sequences of the invention can be obtained by several methods. For example, the DNA can be isolated using hybridization or computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; 4) computer searches of sequence databases for similar sequences, and the like.

In yet another preferred embodiment, the present invention provides isolated nucleic acids including nucleotide sequences comprising or derived from HDAC7 genes and/or encoding polypeptides comprising or derived from HDAC7 proteins. Thus, the present invention provides isolated nucleic acids corresponding to alleles and homologues, as well as the various above-described recombinant constructs derived from these sequences, by means which are well known in the art. Two polynucleotides or polypeptides are said to be "homologous" or "identical" if the sequence of nucleotides or amino acid residues in the two sequences is the same when aligned for maximum correspondence. Optimal alignment of sequences for comparison may be conducted by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci.* (U.S.A.), 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

Standard hybridization screening or PCR techniques may be employed (as used, for example, in the identification of the HDAC7 gene) to identify and/or isolate such allelic and homologous sequences using relatively short gene sequences. The sequences may include 8 or fewer nucleotides depending upon the nature of the target sequences, the method employed, and the specificity required. Future technological developments may allow the advantageous use of even shorter sequences. With current technology, at least 8, and up to about 50 contiguous nucleotides, preferably 9–25, and more preferably 18–24 contiguous nucleotides from an HDAC7 sequence can be employed in such techniques. These sequences may be chosen from those disclosed herein, or may be derived from other allelic or heterospecific homologues enabled herein. When probing mRNA or screening cDNA libraries, probes and primers from coding sequences (rather than introns) are preferably employed, and sequences which are omitted in alternative splice variants typically are avoided unless it is specifically desired to identify those variants. Allelic variants of the invention genes may be expected to hybridize to the disclosed sequences under stringent hybridization conditions, as defined herein, whereas lower stringency may be employed to identify heterospecific homologues.

Stringent hybridization conditions is a term of art understood by those of ordinary skill in the art. For any given nucleic acid sequence, stringent hybridization conditions are those conditions of temperature, chaotrophic acids, buffer, and ionic strength which will permit hybridization of that nucleic acid sequence to its complementary sequence and not to substantially different sequences. The exact conditions which constitute "stringent" conditions depend upon the nature of the nucleic acid sequence, the length of the sequence, and the frequency of occurrence of subsets of that sequence within other non-identical sequences. By varying hybridization conditions from a level of stringency at which non-specific hybridization occurs to a level at which only specific hybridization is observed, one of ordinary skill in the art can, without undue experimentation, determine conditions which will allow a given sequence to hybridize only with complementary sequences. Suitable ranges of such stringency conditions are described in Krause and Aaronson (1991) Methods in Enzymology, 200:546–556. Hybridization conditions, depending upon the length and commonality of a sequence, may include temperatures of 20° C.–65° C., and ionic strengths from 5× to 0.1×SSC. Highly stringent hybridization conditions may include temperatures as low as 40–42° C. (when denaturants such as formamide are included) or up to 60–65° C., with ionic strengths as low as 0.1×SSC. These ranges, however, are only illustrative and, depending upon the nature of the target sequence, and possible future technological developments, may be more stringent than necessary. Less than stringent conditions are employed to isolate nucleic acid sequences that are substantially similar, allelic or homologous to any given sequence.

In another embodiment, the present invention provides for isolated nucleic acids which include subsets of the sequences or their complements. As noted above, such sequences will have utility as probes and PCR primers in the identification and isolation of allelic and homologous variants of the invention genes. Subsequences corresponding to the polymorphic regions of HDAC7, as described above, will also have particular utility in screening and/or genotyping individuals for diagnostic purposes, as described below. In addition, and also as described below, such subsets will have utility for encoding (1) fragments of HDAC7 proteins for inclusion in fusion proteins, (2) fragments which comprise functional domains of HDAC7 proteins for use in binding studies, (3) fragments of HDAC7 proteins which may be used as immunogens to raise antibodies against HDAC7 proteins, and (4) fragments of HDAC7 which may act as competitive inhibitors or as mimetics of HDAC7 to inhibit or mimic their physiological functions. Finally, such subsets may encode or represent complementary or antisense sequences which can hybridize to HDAC7 genes or mRNA transcripts under physiological conditions to inhibit the transcription or translation of those sequences. Therefore, depending upon the intended use, the present invention provides nucleic acid subsequences of the invention genes which may have lengths varying from 8–10 nucleotides (e.g., for use as PCR primers) to nearly the full size of the HDAC7 genomic or cDNAs. Thus, the present invention provides isolated nucleic acids comprising sequences corresponding to at least 8–10, preferably 15, and more preferably at least 20 consecutive nucleotides of the HDAC7 genes, as disclosed or otherwise enabled herein, or to their complements. As noted above, however, shorter sequences may be useful with different technologies.

In a further embodiment, the present invention provides nucleic acids in which the coding sequences, with or without introns or recombinantly engineered as described above, are operably joined to endogenous or exogenous 5' and/or 3' regulatory regions. The endogenous regulatory regions of the HDAC7 gene are described and disclosed in detail herein. Using the present disclosure and standard genetic techniques (e.g., PCR extensions, targeting gene walking), one of ordinary skill in the art is also now enabled to clone the corresponding HDAC7 5' and/or 3' endogenous regulatory regions. Similarly, allelic variants of the HDAC7 endogenous regulatory regions, as wells as endogenous regulatory regions from other mammalian homologues, are similarly enabled without undue experimentation. Alternatively, exogenous regulatory regions (i.e., regulatory regions from a different conspecific gene or a heterospecific regulatory region) may be operably joined to the HDAC7 coding sequences in order to drive expression. Appropriate 5' regulatory regions will include promoter elements and may also include additional elements such as operator or enhancer sequences, ribosome binding sequences, RNA capping sequences, and the like. The regulatory region may be selected from sequences that control the expression of genes of prokaryotic or eukaryotic cells, their viruses, and combinations thereof. Such regulatory regions include, but are not limited to, the lac system, the trp system, the tac system and the trc system; major operator and promoter regions of phage .lambda.; the control region of the fd coat protein; early and late promoters of SV40; promoters derived from polyoma, adenovirus, retrovirus, baculovirus, and simian virus; 3-phosphoglycerate kinase promoter; yeast acid phosphatase promoters; yeast alpha-mating factors; promoter elements of other eukaryotic genes expressed in neurons or other cell types; and combinations thereof. In particular, regulatory elements may be chosen which are inducible or repressible (e.g., the β-galactosidase promoter) to allow for controlled and/or manipulable expression of the invention genes in cells with these nucleic acids. Alternatively, HDAC7 coding regions may be operably joined with regulatory elements which provide for tissue specific expression in multicellular organisms. Such constructs are particularly useful for the production of transgenic organisms to cause expression of HDAC7 genes only in appropriate tissues. The choice of appropriate regulatory regions is within the ability and discretion of one of ordinary skill in the art and the recombinant use of many such regulatory regions is now established in the art.

As used herein, a "transformed cell" is a cell into which (or into an ancestor of which) has been introduced, by means of recombinant DNA techniques, a nucleic acid molecule of interest. The nucleic acid of interest will typically encode a peptide or protein. The transformed cell may express the sequence of interest or may be used only to propagate the sequence. The term "transformed" may be used herein to embrace any method of introducing exogenous nucleic acids including, but not limited to, transformation, transfection, electroporation, microinjection, viral-mediated transfection, and the like.

In still another embodiment, the present invention provides isolated nucleic acids in the form of recombinant DNA constructs in which a marker or reporter gene (e.g., β-galactosidase, luciferase) is operably joined to the 5' regulatory region of a HDAC7 gene such that expression of the marker gene is under the control of the HDAC7 regulatory sequences. Using the HDAC7 regulatory regions disclosed or otherwise enabled herein, including regulatory regions from HDAC7 and HDAC7 genes from human and other mammalian species, one of ordinary skill in the art is now enabled to produce such constructs. As discussed more fully below, such isolated nucleic acids may be used to produce cells, cell lines or transgenic animals which are useful in the identification of compounds which can, directly or indirectly, differentially affect the expression of HDAC7.

The nucleic acids encoding the HDAC7-interacting peptides or proteins of the present invention may be employed in essentially all of the embodiments described above with respect to HDAC7. Thus, nucleic acids encoding HDAC7-interacting peptides are provided which include genomic or cDNA sequences; minigenes with some or all introns removed; subsequences with utility for encoding (1) fragments of HDAC7-interacting proteins for inclusion in fusion proteins, (2) fragments which comprise functional domains of HDAC7-interacting proteins for use in binding studies, (3) fragments of HDAC7-interacting proteins which may be used as immunogens to raise antibodies against HDAC7-interacting proteins, and (4) fragments of HDAC7-interacting proteins which may act as competitive inhibitors or as mimetics of their physiological interaction with HDAC7; sequences operably joined to endogenous or exogenous regulatory elements; sequences joined inframe with other coding sequences to encode a fusion protein (e.g., as in the yeast two-hybrid system); etc.

Finally, the isolated nucleic acids of the present invention include any of the above-described sequences when included in vectors. Appropriate vectors include cloning vectors and expression vectors of all types, including plasmids, phagemids, cosmids, episomes, and the like, as well as integration vectors. The vectors may also include various marker genes (e.g., antibiotic resistance or susceptibility genes) which are useful in identifying cells successfully transformed therewith. In addition, the vectors may include regulatory sequences to which the nucleic acids of the invention are operably joined, and/or may also include coding regions such that the nucleic acids of the invention, when appropriately ligated into the vector, are expressed as fusion proteins. Such vectors may also include vectors for use in yeast "two hybrid," baculovirus, and phage-display systems. The vectors may be chosen to be useful for prokaryotic, eukaryotic or viral expression, as needed or desired for the particular application. For example, vaccinia virus vectors or simian virus vectors with the SV40 promoter (e.g., pSV2), or Herpes simplex virus or adeno-associated virus may be useful for transfection of mammalian cells including neurons in culture or in vivo, and the baculovirus vectors may be used in transfecting insect cells (e.g., butterfly cells). A great variety of different vectors are now commercially available and otherwise known in the art, and the choice of an appropriate vector is within the ability and discretion of one of ordinary skill in the art.

In another embodiment of the present invention, there are provided substantially pure protein preparations including polypeptides comprising or derived from HDAC7 proteins. The HDAC7 protein sequences of the invention include the specifically disclosed sequences, variants of these sequences resulting from alternative mRNA splicing, allelic variants of these sequences, muteins of these sequences and homologous or orthologous variants of these sequences. Thus, for example, the invention provides amino acid sequences from the HDAC7 protein. The present invention also provides allelic variants and homologous or orthologous proteins by providing methods by which such variants may be routinely obtained. The present invention also specifically provides for mutant or disease-causing variants of HDAC7 by disclosing a number of specific mutant sequences and by providing methods by which other such variants may be routinely obtained. Because the proteins of the invention may be used in a variety of diagnostic, therapeutic and recombinant applications, various subsets of HDAC7 protein sequences and combinations of HDAC7 protein sequences with heterologous sequences are also provided. For example, for use as immunogens or in binding assays, subsets of the HDAC7 protein sequences, including both normal and mutant sequences, are provided. Such protein sequences may comprise a small number of consecutive amino acid residues from the sequences which are disclosed or otherwise enabled herein but preferably include at least 4–8, and preferably at least 9–15 consecutive amino acid residues from a HDAC7 sequence. Other preferred subsets of the HDAC7 protein sequences include those corresponding to one or more of the functional domains or antigenic determinants of the HDAC7 proteins and, in particular, may include either normal (wild-type) or mutant sequences. The invention also provides for various protein constructs in which HDAC7 sequences, either complete or subsets, are joined to exogenous sequences to form fusion proteins and the like. In accordance with these embodiments, the present invention also provides for methods of producing all of the above described proteins which comprise, or are derived from, HDAC7.

The present invention provides for substantially pure preparations of the HDAC7 proteins (see, e.g., SEQ ID NO:2, corresponding to mouse HDAC7 (mHDAC7)), functional equivalents, fragments of the HDAC7 proteins, and fusion proteins including HDAC7 or fragments thereof. The proteins, fragments and fusions have utility, as described herein, in the generation of antibodies to normal and mutant HDAC7s, in the identification of HDAC7 binding proteins, and in diagnostic and therapeutic methods. Therefore, depending upon the intended use, the present invention provides substantially pure proteins or peptides comprising amino acid sequences which are subsequences of the complete HDAC7 proteins and which may have lengths varying from 4–10 amino acids (e.g., for use as immunogens), or 10–100 amino acids (e.g., for use in binding assays), to the complete HDAC7 proteins. Thus, the present invention provides substantially pure proteins or peptides comprising sequences corresponding to at least 4–5, preferably 6–10, and more preferably at least 50 to 100 consecutive amino acids of HDAC7 proteins, as disclosed or otherwise enabled herein.

As used herein with respect to proteins (including antibodies) or other preparations, the term "substantially pure" means a preparation which is at least 60% by weight (dry weight) the compound of interest. Preferably the preparation is at least 75%, more preferably at least 90%, and most preferably at least 99%, by weight the compound of interest. Purity can be measured by any appropriate method, e.g., column chromatography, gel electrophoresis, or HPLC analysis. With respect to proteins, including antibodies, if a preparation includes two or more different compounds of interest (e.g., two or more different antibodies, immunogens, functional domains, or other polypeptides of the invention), a "substantially pure" preparation means a preparation in which the total weight (dry weight) of all the compounds of interest is at least 60% of the total dry weight. Similarly, for such preparations containing two or more compounds of interest, it is preferred that the total weight of the compounds of interest be at least 75%, more preferably at least 90%, and most preferably at least 99%, of the total dry weight of the preparation. Finally, in the event that the protein of interest is mixed with one or more other proteins (e.g., serum albumin) or compounds (e.g., diluents, excipients, salts, polysaccharides, sugars, lipids) for purposes of administration, stability, storage, and the like, such other proteins or compounds may be ignored in calculation of the purity of the preparation.

As used herein in describing gene sequences and amino acid sequences, the term "functional equivalent" means that a recited sequence need not be identical to a particularly disclosed sequence of the SEQ ID NOs but need only provide a sequence which functions biologically and/or chemically as the equivalent of the disclosed sequence.

As used herein, a "substantially identical" amino acid sequence is an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (measured, e.g., as described herein). Preferably, such a sequence is at least 85%, more preferably 90%, and most preferably 95% identical at the amino acid level to the sequence of the protein or peptide to which it is being compared. For nucleic acids, the length of comparison sequences will generally be at least 50 nucleotides, preferably at least 60 nucleotides, more preferably at least 75 nucleotides, and most preferably 110 nucleotides. A "substantially identical" nucleic acid sequence codes for a substantially identical amino acid sequence as defined above.

The proteins or peptides of the invention may be isolated and purified by any of a variety of methods selected on the basis of the properties revealed by their protein sequences. For example, purification can be achieved using standard protein purification procedures including, but not limited to, gel-filtration chromatography, ion-exchange chromatography, high-performance liquid chromatography (RP-HPLC, ion-exchange HPLC, size-exclusion HPLC, high-performance chromatofocusing chromatography, hydrophobic interaction chromatography, immunoprecipitation, or immunoaffinity purification. Gel electrophoresis (e.g., PAGE, SDS-PAGE) can also be used to isolate a protein or peptide based on its molecular weight, charge properties and hydrophobicity.

In accordance with another embodiment of the present invention, there are provided polyclonal and monoclonal antibodies that selectively bind to invention polypeptides. Also provided are antibody fragments, including Fab fragments, F(ab')$_2$, and single chain antibody fragments, which selectively bind to HDAC7, or to specific antigenic determinants of HDAC7. Also provided are methods for the production and use of invention antibodies. The antibodies of the present invention may be raised in mouse, rabbit, goat or other suitable animals, or may be produced recombinantly in cultured cells such as hybridoma cell lines. Preferably, the antibodies are raised against HDAC7 sequences comprising at least 4–8, and preferably at least 9–15 consecutive amino acid residues from a HDAC7 sequence. The antibodies of the invention may be used in the various diagnostic, therapeutic and technical applications described herein.

Of particular importance, by identifying the functional domains of HDAC7 and the polymorphic regions associated with associated diseases and disorders, the present invention provides antibodies, and methods of making antibodies, which will selectively bind to and, thereby, identify and/or distinguish normal and mutant (i.e., pathogenic) forms of the HDAC7 proteins. The antibodies of the invention have utility as laboratory reagents for, inter alia, immunoaffinity purification of HDAC7, Western blotting to identify cells or tissues expressing HDAC7, and immunocytochemistry or immunofluorescence techniques to establish the subcellular location of the protein.

As used herein with respect to antibodies, an antibody is said to "selectively bind" to a target if the antibody recognizes and binds the target of interest but does not substantially recognize and bind other molecules in a sample, e.g., a biological sample, which includes the target of interest.

The antibodies of the invention may be generated using the entire HDAC7 proteins of the present invention or using any HDAC7 epitope which is characteristic of that protein and which substantially distinguishes it from other host proteins. Such epitopes may be identified by comparing sequences of, for example, HDAC7 in comparison with the other HDAC members. On the other hand, antibodies against highly conserved domains are expected to have the greatest utility for purification or identification of HDAC7.

HDAC7 immunogen preparations may be produced from crude extracts (e.g., membrane fractions of cells highly expressing the proteins), from proteins or peptides substantially purified from cells which naturally or recombinantly express them or, for short immunogens, by chemical peptide synthesis. As used herein, a HDAC7 immunogen shall be defined as a preparation including a peptide comprising at least 4–8, and preferably at least 9–15 consecutive amino acid residues of the HDAC7 proteins, as disclosed or otherwise enabled herein. Sequences of fewer residues may, of course, also have utility depending upon the intended use and future technological developments. Therefore, any HDAC7 derived sequences which are employed to generate antibodies to HDAC7 should be regarded as HDAC7 immunogens.

The antibodies of the invention may be polyclonal or monoclonal, or may be antibody fragments, including Fab fragments, F(ab')$_2$, and single chain antibody fragments. In addition, after identifying useful antibodies by invention methods, recombinant antibodies may be generated, including any of the antibody fragments listed above, as well as humanized antibodies based upon non-human antibodies to HDAC7 proteins. In light of the present disclosures of HDAC7 proteins, as well as the characterization of other HDAC7s enabled herein, one of ordinary skill in the art may produce the above-described antibodies by any of a variety of standard means well known in the art. For an overview of antibody techniques, see Antibody Engineering: A Practical Guide, Borrebaek, ed., W.H. Freeman & Company, NY (1992), or Antibody Engineering, 2nd Ed., Borrebaek, ed., Oxford University Press, Oxford (1995).

As a general matter, polyclonal antibodies may be generated by first immunizing a mouse, rabbit, goat or other suitable animal with the HDAC7 immunogen in a suitable carrier. To increase the immunogenicity of the preparation, the immunogen may be coupled to a carrier protein or mixed with an adjuvant (e.g., Freund's adjuvant). Booster injections, although not necessary, are recommended. After an appropriate period to allow for the development of a humoral response, preferably several weeks, the animals may be bled and the sera may be purified to isolate the immunoglobulin component.

Similarly, as a general matter, monoclonal anti-HDAC7 antibodies may be produced by first injecting a mouse, rabbit, goat or other suitable animal with a HDAC7 immunogen in a suitable carrier. As above, carrier proteins or adjuvants may be utilized and booster injections (e.g., bi- or tri-weekly over 8–10 weeks) are recommended. After allowing for development of a humoral response, the animals are sacrificed and their spleens are removed and resuspended in, for example, phosphate buffered saline (PBS). The spleen cells serve as a source of lymphocytes, some of which are producing antibody of the appropriate specificity. These cells are then fused with an immortalized cell line (e.g., myeloma), and the products of the fusion are plated into a number of tissue culture wells in the presence of a selective agent such as HAT. The wells are serially screened and replated, each time selecting cells making useful antibody. Typically, several screening and replating procedures are carried out until over 90% of the wells contain single clones which are positive for antibody production. Monoclonal antibodies produced by such clones may be purified by standard methods such as affinity chromatography using Protein A Sepharose, by ion-exchange chromatography, or by variations and combinations of these techniques.

The antibodies of the invention may be labeled or conjugated with other compounds or materials for diagnostic and/or therapeutic uses. For example, they may be coupled to radionuclides, fluorescent compounds, or enzymes for imaging or therapy, or to liposomes for the targeting of compounds contained in the liposomes to a specific tissue location.

In accordance with another embodiment of the present invention, there are provided host cells that have been transfected or otherwise transformed with one or more invention nucleic acids. The cells may be transformed merely for purposes of propagating the nucleic acid constructs of the invention, or may be transformed so as to express the HDAC7 sequences. The transformed cells of the invention may be used in assays to identify proteins and/or other compounds which affect normal or mutant HDAC7 expression, which interact with the normal or mutant HDAC7 proteins, and/or which modulate the function or effects of the normal or mutant proteins, or to produce the HDAC7 proteins, fusion proteins, functional domains, antigenic determinants, and/or antibodies of the invention. Transformed cells may also be implanted into hosts, including humans, for therapeutic or other reasons. Preferred host cells include mammalian cells from neuronal, fibroblast, bone marrow, spleen, organotypic or mixed cell cultures, as well as bacterial, yeast, nematode, insect and other invertebrate cells. For uses as described below, preferred cells also include embryonic stem cells, zygotes, gametes, and germ line cells.

In another embodiment of the present invention, there are also provided cells and cell lines, both prokaryotic and eukaryotic, which have been transformed or transfected with the nucleic acids of the present invention so as to cause clonal propagation of those nucleic acids and/or expression of the proteins or peptides encoded thereby. Such cells or cell lines will have utility both in the propagation and production of the nucleic acids and proteins of the present invention but also, as further described herein, as model systems for diagnostic and therapeutic assays. As used herein, the term "transformed cell" is intended to embrace any cell, or the descendant of any cell, into which has been introduced any of the nucleic acids of the invention, whether by transformation, transfection, infection, or other means. Methods of producing appropriate vectors, transforming cells with those vectors, and identifying transformants are well known in the art and are only briefly reviewed here (see, for example, Sambrook et al. (1989) Molecular Cloning: A Laboratory Manual, 2nd ed., Cold Spring Harbor Laboratory Press, Cold Spring Harbor, N.Y.).

Prokaryotic cells useful for producing the transformed cells of the invention include members of the bacterial genera Escherichia (e.g., *E. coli*), Pseudomonas (e.g., *P. aeruginosa*), and Bacillus (e.g., *B. subtillus, B. stearothermophilus*), as well as many others well known and frequently used in the art. Prokaryotic cells are particularly useful for the production of large quantities of the proteins or peptides of the invention (e.g., normal or mutant HDAC7s, fragments of HDAC7, fusion proteins of HDAC7). Bacterial cells (e.g., *E. coli*) may be used with a variety of expression vector systems including, for example, plasmids with the T7 RNA polymerase/promoter system, bacteriophage λ regulatory sequences, or M13 Phage mGPI-2. Bacterial hosts may also be transformed with fusion protein vectors which create, for example, lacZ, trpE, maltose-binding protein, poly-His tags, or glutathione-S-transferase fision proteins. All of these, as well as many other prokaryotic expression systems, are well known in the art and widely available commercially (e.g., pGEX-27 (Amrad, USA) for GST fusions).

Eukaryotic cells and cell lines useful for producing transformed cells of the invention include mammalian cells and cell lines (e.g., PC 12, COS, CHO, fibroblasts, myelomas, neuroblastomas, hybridomas, human embryonic kidney 293, oocytes, embryonic stem cells), insect cells lines (e.g., using baculovirus vectors such as pPbac or pMbac (Stratagene, La Jolla, Calif.)), yeast (e.g., using yeast expression vectors such as pYESHIS (Invitrogen, San Diego, Calif.)), and fungi. Eukaryotic cells are particularly useful for embodiments in which it is necessary that the HDAC7 proteins, or functional fragments or variants thereof, or muteins thereof, perform the functions and/or undergo the intracellular interactions associated with either the normal or mutant proteins. Thus, for example, transformed eukaryotic cells are preferred for use as models of HDAC7 function or interaction, and assays for screening candidate therapeutics preferably employ transformed eukaryotic cells.

To accomplish expression in eukaryotic cells, a wide variety of vectors have been developed and are commercially available which allow inducible (e.g., LacSwitch expression vectors, Stratagene, La Jolla, Calif.) or cognate (e.g., pcDNA3 vectors, Invitrogen, San Diego, Calif.) expression of HDAC7 nucleotide sequences under the regulation of an artificial promoter element. Such promoter elements are often derived from CMV or SV40 viral genes, although other strong promoter elements which are active in eukaryotic cells can also be employed to induce transcription of nucleotide sequences. Typically, these vectors also contain an artificial polyadenylation sequence and 3' LTR which can also be derived from exogenous viral gene sequences or from other eukaryotic genes. Furthermore, in some constructs, artificial, non-coding, spliceable introns and exons are included in the vector to enhance expression of the nucleotide sequence of interest (in this case, HDAC7 sequences). These expression systems are commonly available from commercial sources and are typified by vectors such as pcDNA3 and pZeoSV (Invitrogen, San Diego, Calif.). Both of the latter vectors have been successfully used to cause expression of HDAC7 proteins in transfected COS, CHO, and PC12 cells (Levesque et al. 1996). Innumerable commercially-available as well as custom-designed expression vectors are available from commercial sources to allow expression of any desired HDAC7 transcript in more or less any desired cell type, either constitutively or after exposure to a certain exogenous stimulus (e.g., withdrawal of tetracycline or exposure to IPTG).

Vectors may be introduced into the recipient or "host" cells by various methods well known in the art including, but not limited to, calcium phosphate transfection, strontium phosphate transfection, DEAE dextran transfection, electroporation, lipofection (e.g., Dosper Liposomal transfection reagent, Boehringer Mannheim, Germany), microinjection, ballistic insertion on microbeads, protoplast fusion or, for viral or phage vectors, by infection with the recombinant virus or phage.

In accordance with another embodiment of the present invention, there are provided transgenic animal models for neoplasia and other diseases or disorders associated with mutations in HDAC7 genes. The animal may be essentially any mammal, including rats, mice, hamsters, guinea pigs, rabbits, dogs, cats, goats, sheep, pigs, and non-human primates. In addition, invertebrate models, including nematodes and insects, may be used for certain applications. The animal models are produced by standard transgenic methods including microinjection, transfection, or by other forms of transformation of embryonic stem cells, zygotes, gametes, and germ line cells with vectors including genomic or cDNA fragments, minigenes, homologous recombination vectors, viral insertion vectors and the like. Suitable vectors include vaccinia virus, adenovirus, adeno associated virus, retrovirus, liposome transport, neuraltropic viruses, and Herpes simplex virus. The animal models may include transgenic sequences comprising or derived from HDAC7, including normal and mutant sequences, intronic, exonic and untranslated sequences, and sequences encoding subsets of HDAC7 such as functional domains.

The major types of animal models provided include: (1) Animals in which a normal human HDAC7 gene has been recombinantly introduced into the genome of the animal as an additional gene, under the regulation of either an exogenous or an endogenous promoter element, and as either a minigene or a large genomic fragment; in which a normal human HDAC7 gene has been recombinantly substituted for one or both copies of the animal's homologous HDAC7 gene by homologous recombination or gene targeting; and/or in which one or both copies of one of the animal's homologous HDAC7 genes have been recombinantly "humanized" by the partial substitution of sequences encoding the human homologue by homologous recombination or gene targeting. (2) Animals in which a mutant human HDAC7 gene has been recombinantly introduced into the genome of the animal as an additional gene, under the regulation of either an exogenous or an endogenous promoter element, and as either a minigene or a large genomic fragment; in which a mutant human HDAC7 gene has been recombinantly substituted for one or both copies of the animal's homologous HDAC7 gene by homologous recombination or gene targeting; and/or in which one or both copies of one of the animal's homologous HDAC7 genes have been recombinantly "humanized" by the partial substitution of sequences encoding a mutant human homologue by homologous recombination or gene targeting. (3) Animals in which a mutant version of one of that animal's HDAC7 genes has been recombinantly introduced into the genome of the animal as an additional gene, under the regulation of either an exogenous or an endogenous promoter element, and as either a minigene or a large genomic fragment; and/or in which a mutant version of one of that animal's HDAC7 genes has been recombinantly substituted for one or both copies of the animal's homologous HDAC7 gene by homologous recombination or gene targeting. (4) "Knock-out" animals in which one or both copies of one of the animal's HDAC7 genes have been partially or completely deleted by homologous recombination or gene targeting, or have been inactivated by the insertion or substitution by homologous recombination or gene targeting of exogenous sequences. In preferred embodiments, a transgenic mouse model for neoplasia has a transgene encoding a normal human HDAC7 protein, a mutant human or murine HDAC7 protein, or a humanized normal or mutant murine HDAC7 protein generated by homologous recombination or gene targeting.

Animal species suitable for use in the animal models of the present invention include, but are not limited to, rats, mice, hamsters, guinea pigs, rabbits, dogs, cats, goats, sheep, pigs, and nonhuman primates (e.g., Rhesus monkeys, chimpanzees). For initial studies, transgenic rodents (e.g., mice) are preferred due to their relative ease of maintenance and shorter life spans. Indeed, as noted above, transgenic yeast or invertebrates (e.g., nematodes, insects) may be preferred for some studies because they will allow for even more rapid and inexpensive screening. Transgenic non-human primates, however, may be preferred for longer term studies due to their greater similarity to humans and their higher cognitive abilities.

The techniques of generating transgenic animals, as well as the techniques for homologous recombination or gene targeting, are now widely accepted and practiced. A laboratory manual on the manipulation of the mouse embryo, for example, is available detailing standard laboratory techniques for the production of transgenic mice (Hogan et al. (1986) Manipulating the Mouse Embryo, Cold Spring Harbor Laboratory Press, Cold Spring Harbor, N.Y.). To create a transgene, the target sequence of interest (e.g., normal or mutant HDAC7 sequences, normal or mutant HDAC7-interacting protein sequences) are typically ligated into a cloning site located downstream of some promoter element which will regulate the expression of RNA from the sequence. Downstream of the coding sequence, there is typically an artificial polyadenylation sequence. An alternate approach to creating a transgene is to use an endogenous HDAC7 or HDAC7-interacting protein gene promoter and regulatory sequences to drive expression of the transgene.

In accordance with yet another embodiment of the present invention, there are provided methods for identifying proteins and other compounds which bind to, or otherwise directly interact with, the HDAC7. The proteins and compounds include endogenous cellular components which interact with the HDAC7 in vivo and which, therefore, provide new targets for pharmaceutical and therapeutic interventions, as well as recombinant, synthetic and otherwise exogenous compounds which may have HDAC7 binding capacity and, therefore, may be candidates for pharmaceutical agents. Thus, in one aspect of this embodiment, cell lysates or tissue homogenates (e.g., human homogenates, lymphocyte lysates) may be screened for proteins or other compounds which bind to one of the normal or mutant HDAC7s. Alternatively, any of a variety of exogenous compounds, both naturally occurring and/or synthetic (e.g., libraries of small molecules or peptides), may be screened for HDAC7 binding capacity.

In each of the forgoing aspects of this embodiment, an assay is conducted to detect binding between a "HDAC7 component" and some other moiety. The HDAC7 component" in these assays may be any polypeptide comprising or derived from a normal or mutant HDAC7 protein, including functional domains or antigenic determinants of the HDAC7 fusion proteins. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of HDAC7 components and bound proteins or other compounds by immunoprecipitation; (3) BIAcore analysis; and (4) the two-hybrid systems.

Small molecules are particularly preferred as candidate compounds in this context because they are more readily absorbed after oral administration, have fewer potential antigenic determinants, and/or are more likely to cross (or more effectively) the cellular/nuclear membrane than larger molecules such as nucleic acids or proteins.

The effect of agents which bind to HDAC7 (normal or mutant forms) can be monitored either by the direct monitoring of this binding using instruments (e.g., BIAcore, LKB Pharmacia, Sweden) to detect this binding by, for example, a change in fluorescence, molecular weight, or concentration of either the binding agent or HDAC7 component, either in a soluble phase or in a substrate-bound phase.

In addition, once identified by the methods described above, the candidate compounds may also serve as "lead compounds" in the design and development of new pharmaceuticals. For example, as in well known in the art, sequential modification of small molecules (e.g., amino acid residue replacement with peptides; functional group replacement with peptide or non-peptide compounds) is a standard approach in the pharmaceutical industry for the development of new pharmaceuticals. Such development generally proceeds from a "lead compound" which is shown to have at least some of the activity (e.g., HDAC7 binding or blocking ability) of the desired pharmaceutical. In particular, when one or more compounds having at least some activity of interest (e.g., modulation of HDAC7 activity) are identified, structural comparison of the molecules can greatly inform the skilled practitioner by suggesting portions of the lead compounds which should be conserved and portions which may be varied in the design of new candidate compounds. Thus, the present invention also provides a means of identifying lead compounds which may be sequentially modified to produce new candidate compounds for use in the treatment of cancer. These new compounds then may be tested both for HDAC7-binding or blocking (e.g., in the binding assays described above) and for therapeutic efficacy (e.g., in the animal models described herein). This procedure may be iterated until compounds having the desired therapeutic activity and/or efficacy are identified.

The proteins or other compounds identified by these methods may be purified and characterized by any of the standard methods known in the art. Proteins may, for example, be purified and separated using electrophoretic (e.g., SDS-PAGE, 2D PAGE) or chromatographic (e.g., HPLC) techniques and may then be microsequenced. For proteins with a blocked N-terminus, cleavage (e.g., by CNBr and/or trypsin) of the particular binding protein is used to release peptide fragments. Further purification/characterization by HPLC and microsequencing and/or mass spectrometry by conventional methods provides internal sequence data on such blocked proteins. For non-protein compounds, standard organic chemical analysis techniques (e.g., IR, NMR and mass spectrometry; functional group analysis; X-ray crystallography) may be employed to determine their structure and identity.

Methods for screening cellular lysates, tissue homogenates, or small molecule libraries for candidate HDAC7-binding molecules are well known in the art and, in light of the present disclosure, may now be employed to identify compounds which bind to normal or mutant HDAC7 components or which modulate HDAC7 activity as defined by non-specific measures (e.g., changes, in transcription, chromatid formation/disruption) or by specific measures (e.g., peptide production or changes in the expression of other downstream genes which can be monitored by differential display, 2D gel electrophoresis, differential hybridization, or SAGE methods). The preferred methods involve variations on the following techniques: (1) direct extraction by affinity chromatography; (2) co-isolation of HDAC7 components and bound proteins or other compounds by immunoprecipitation; (3) the Biomolecular Interaction Assay (BIAcore); and (4) the yeast two-hybrid systems.

As will be clear to one of ordinary skill in the art, there are numerous other methods of screening individual proteins or other compounds, as well as large libraries of proteins or other compounds (e.g., phage display libraries and cloning systems from Stratagene, La Jolla, Calif.) to identify molecules which bind to normal or mutant HDAC7 components. All of these methods comprise the step of mixing a normal or mutant HDAC7 protein, fusion, or fragment with test compounds, allowing for binding (if any), and assaying for bound complexes. All such methods are now enabled by the present disclosure of substantially pure HDAC7s, substantially pure HDAC7 functional domain fragments, HDAC7 fusion proteins, HDAC7 antibodies, and methods of making and using the same.

The ability to disrupt specific HDAC7 interactions with other proteins is potentially of great therapeutic value, and will be important in understanding the etiology of cancers and in identifying additional targets for therapy. The methods used to identify compounds which disrupt HDAC7 interactions may be applied equally well to interactions involving either normal or mutant HDAC7s and either normal or mutant interacting proteins.

Assays for compounds which can disrupt HDAC7 interactions may be performed by any of a variety of methods well known in the art. In essence, such assays will parallel those assays for identifying HDAC7-interacting proteins and compounds. Thus, once a HDAC7-interacting protein is identified by any method, that method or an equivalent method may be performed in the presence of candidate compounds to identify compounds which disrupt the interaction. Thus, for example, the assay may employ methods including (1) affinity chromatography; (2) immunoprecipitation; (3) the Biomolecular Interaction Assay (BIAcore); or (4) the yeast two-hybrid systems. Such assays can be developed using either normal or mutant purified HDAC7 proteins, and/or either normal or mutant and purified HDAC7-interacting proteins.

These assays may be used to screen many different types of compounds for their disruptive effect on the interactions of HDAC7. For example, the compounds may belong to a library of synthetic molecules, or be specifically designed to disrupt the interaction. The compounds may also be peptides corresponding to the interacting domain of either protein. This type of assay can be used to identify compounds that disrupt a specific interaction between a given HDAC7 variant and a given interacting protein. In addition, compounds that disrupt all interactions with HDAC7s may be identified. For example, a compound that specifically disrupts the folding of HDAC7 proteins would be expected to disrupt all interactions between HDAC7s and other proteins. Alternatively, this type of disruption assay can be used to identify compounds which disrupt only a range of different HDAC7 interactions, or only a single HDAC7 interaction.

In accordance with a further embodiment of the present invention, there are provided methods of identifying proteins, small molecules and other compounds capable of modulating the activity of normal or mutant histone deacetylases, class I and/or class II, preferably HDAC7. In a particular aspect of the present invention, there are provided methods for identifying compounds capable of modulating specifically class I or class II histone deacetylases, more preferably, HDAC7. Using normal cells or animals, the transformed cells and animal models of the present invention, or cells obtained from subjects bearing normal or mutant histone deacetylase genes, e.g., HDAC7 genes, the present invention provides methods of identifying such compounds on the basis of their ability to affect the expression of HDAC7, the intracellular localization of HDAC7, changes in transcription activity, or other metabolic measures, the occurrence or rate of apoptosis or cell death, the levels or pattern of chromatid production, the presence or levels of acytelation of histones, or other biochemical, histological, or physiological markers which distinguish cells bearing normal and mutant HDAC7 sequences. Using the animal models of the invention, methods of identifying such compounds are also provided on the basis of the ability of the compounds to affect behavioral, physiological or histological phenotypes associated with mutations in HDAC7, including cancers.

As used with respect to this embodiment, the term "activity" broadly includes gene and protein expression, HDAC7 protein post-translation processing, trafficking and localization, and any functional activity as described herein, as well as downstream affects of any of these. Therefore, using the transformed cells and transgenic animal models of the present invention, cells obtained from subjects bearing a mutant HDAC7 gene, or animals or human subjects bearing naturally occurring HDAC7 mutations, it is now possible to screen candidate pharmaceuticals and treatments for their therapeutic effects by detecting changes in one or more of these functional characteristics or phenotypic manifestations of normal or mutant HDAC7 expression.

Thus, the present invention provides methods for screening or assaying for proteins, small molecules or other compounds which modulate HDAC7 activity by contacting a cell in vivo or in vitro with a candidate compound and assaying for a change in a marker associated with normal or mutant HDAC7 activity. The marker associated with HDAC7 activity may be any measurable biochemical, physiological, histological and/or behavioral characteristic associated with HDAC7 expression. In particular, useful markers will include any measurable biochemical, physiological, histological and/or behavioral characteristic which distinguishes cells, tissues, animals or individuals bearing at least one mutant HDAC7 gene from their normal counterparts. In addition, the marker may be any specific or non-specific measure of HDAC7 activity. HDAC7 specific measures include measures of HDAC7 expression (e.g., HDAC7 mRNA or protein levels) which may employ the nucleic acid probes or antibodies of the present invention. Non-specific measures include changes in cell physiology which can be monitored on devices such as the cytosensor microphysiometer (Molecular Devices Inc., United States). The activation or inhibition of HDAC7 activity in its mutant or normal form can also be monitored by examining changes in the expression of other genes which are specific to the HDAC7 pathway leading to cancer.

In light of the identification, characterization, and disclosure herein of HDAC7 genes and proteins, HDAC7 nucleic acid probes and antibodies, and HDAC7 transformed cells and transgenic animals of the invention, one of ordinary skill in the art is now enabled by perform a great variety of assays which will detect the modulation of HDAC7 activity by candidate compounds. Particularly preferred and contemplated embodiments are discussed in some detail below.

Accumulating evidence points to a connection between cancer and transcriptional control by histone acetylation and deacetylation (Fenrick R, Hiebert S W, J Cell Biochem (Suppl 1998);30–31:194–202). This is particularly true with regard to the acute leukemias, many of which are caused by fusion proteins that have been created by chromosomal translocations. Genetic rearrangements that disrupt the retinoic acid receptor-alpha and acute myeloid leukemia-1 genes create fusion proteins that block terminal differentiation of hematopoietic cells by repressing transcription. These fusion proteins interact with nuclear hormone co-repressors, which recruit histone deacetylases to promoters to repress transcription. This finding suggests that proteins within the histone deacetylase complexes may be potential targets for pharmaceutical intervention in many leukemia patients.

Accordingly, in accordance with another embodiment of the present invention, there are provided methods of screening or identifying proteins, small molecules or other compounds which are capable of inducing or inhibiting the expression of HDAC7 genes and proteins. The assays may be performed in vitro using transformed or non-transformed cells, immortalized cell lines, or in vivo using the transgenic animal models or human subjects enabled herein. In particular, the assays may detect the presence of increased or decreased expression of HDAC7 or other HDAC7-related genes or proteins on the basis of increased or decreased mRNA expression (using, e.g., the nucleic acid probes disclosed and enabled herein), increased or decreased levels of HDAC7-related protein products (using, e.g., the anti-HDAC7 antibodies disclosed and enabled herein), or increased or decreased levels of expression of a marker gene (e.g., β-galactosidase, green fluorescent protein, alkaline phosphatase or luciferase) operably joined to a HDAC7 5' regulatory region in a recombinant construct. Cells known to express a particular HDAC7, or transformed to express a particular HDAC7, are incubated and one or more test compounds are added to the medium. After allowing a sufficient period of time (e.g., 0–72 hours) for the compound to induce or inhibit the expression of the HDAC7, any change in levels of expression from an established baseline may be detected using any of the techniques described herein. In particularly preferred embodiments, the cells are from an immortalized cell line such as a human neuroblastoma, glioblastoma or a hybridoma cell line, or are transformed cells of the invention.

Thus, for example, one may culture cells known to express a particular HDAC7 and add to the culture medium one or more test compounds. After allowing a sufficient period of time (e.g., 0–72 hours) for the compound to induce or inhibit the expression of the HDAC7, any change in levels of expression from an established baseline may be detected using any of the techniques described herein and well known in the art. In particularly preferred embodiments, the cells are from an immortalized cell line such as a human neuroblastoma, glioblastoma or a hybridoma cell line. Using the nucleic acid probes and/or antibodies disclosed and enabled herein, detection of changes in the expression of a HDAC7, and thus identification of the compound as an inducer or repressor of HDAC7 expression, requires only routine experimentation.

In accordance with another embodiment of the present invention, there are provided methods for screening for carriers of HDAC7 alleles associated with mutations in the HDAC7 genes. Screening and/or diagnosis can be accomplished by methods based upon the nucleic acids (including genomic and mRNA/cDNA sequences), proteins, and/or antibodies disclosed and enabled herein, including functional assays designed to detect failure or augmentation of the normal HDAC7 activity and/or the presence of specific new activities conferred by the mutant HDAC7. Thus, screens and diagnostics based upon HDAC7 proteins are provided which detect differences between mutant and normal HDAC7 in electrophoretic mobility, in proteolytic cleavage patterns, in molar ratios of the various amino acid residues, in ability to bind specific antibodies. In addition, screens and diagnostics based upon nucleic acids (gDNA, cDNA or mRNA) are provided which detect differences in nucleotide sequences by direct nucleotide sequencing, hybridization using allele specific oligonucleotides, restriction enzyme digest and mapping (e.g., RFLP, REF-SSCP), electrophoretic mobility (e.g., SSCP, DGGE), PCR mapping, Rnase protection, chemical mismatch cleavage, ligase-mediated detection, and various other methods. Other methods are also provided which detect abnormal processing of HDAC7, or proteins reacting with HDAC7 alterations in HDAC7 transcription, translation, and post-translational modification; alterations in the intracellular and extracellular trafficking of HDAC7 gene products; or abnormal intracellular localization of HDAC7. In accordance with these embodiments, diagnostic kits are also provided which will include the reagents necessary for the above-described diagnostic screens.

The HDAC7 genes and gene products, as well as the HDAC7-derived probes, primers and antibodies, disclosed or otherwise enabled herein, are useful in screening for carriers of alleles associated with cancer, for diagnosis of victims of cancer, all of which are seen to a greater or lesser extent in symptomatic human subjects bearing mutations in HDAC7 or HDAC7 genes or in HDAC7-interacting proteins. Individuals at risk for cancers, such as those with cancers present in the family pedigree, or individuals not previously known to be at risk, may be routinely screened using probes to detect the presence of a mutant HDAC7 gene or protein by a variety of techniques. Diagnosis of inherited cases of these diseases can be accomplished by invention methods. Preferably, the methods and products are based upon the human HDAC7 nucleic acids, proteins or antibodies, as disclosed or otherwise enabled herein.

Trichostatin A (TSA), an inhibitor of the eukaryotic cell cycle and an inducer of morphological reversion of transformed cells, inhibits histone deacetylase (HDAC) at nanomolar concentrations. Recently, trapoxin, oxamflatin, and FR901228, antitumor agents structurally unrelated to TSA, were found to be potent HDAC inhibitors (see, e.g., Archer S Y, Hodin R A. Curr Opin Genet Dev. (1999) 9(2):171–4; Yoshida M, Horinouchi S, Ann N Y Acad Sci (1999) 886:23–36); Zwiebel J A, Leukemia (2000) 14(3):488–90). Changes in the expression of these cell cycle regulators by an increase in histone acetylation may be responsible for cell cycle arrest and antitumor activity by HDAC inhibitors.

Accordingly, in accordance with yet another embodiment of the present invention provides methods and pharmaceutical preparations for use in the treatment of histone deacetylase-associated diseases, e.g., HDAC7-associated diseases such as cancers.

The present invention also provides a basis for therapeutic intervention in diseases which are caused, or which may be caused, by mutations in HDAC7 as well as under/over expression of HDAC7. As detailed above, mutations in hHDAC7 and hHDAC7 genes have been associated with the development of cancers and, therefore, the present invention is particularly directed to the treatment of subjects diagnosed with, or at risk of developing, cancers. Therefore, the present invention is also directed at diseases manifest in other tissues which may arise from mutations, mis-expression, mis-metabolism or other inherited or acquired alterations in HDAC7 genes, gene products and/or activities.

Therapies to treat HDAC7-associated diseases such as cancers may be based upon (1) administration of normal HDAC7 or HDAC7 proteins, (2) gene therapy with normal HDAC7 or HDAC7 genes to compensate for or replace the mutant genes, (3) gene therapy based upon antisense sequences to mutant HDAC7 or HDAC7 genes or which "knock-out" the mutant genes, (4) gene therapy based upon sequences which encode a protein which blocks or corrects the deleterious effects of HDAC7 or HDAC7 mutants, (5) immunotherapy based upon antibodies to normal and/or mutant HDAC7 or HDAC7 proteins, or (6) small molecules (drugs) which alter HDAC7 or HDAC7 expression, block abnormal interactions between mutant forms of HDAC7 or HDAC7 and other proteins or ligands, or which otherwise block the aberrant function of mutant HDAC7 or HDAC7 proteins by altering the structure of the mutant proteins, by enhancing their metabolic clearance, or by inhibiting their function.

In contrast to the prior art, the present disclosure also identifies and partially characterizes a number of human cellular proteins which interact with HDAC7 under physiological conditions, including nuclear co-repressors such as N-CorR or SMRT, or mSin3A, or additional class I and class histone deacetylases (such as HDA, HDB, HDAC1, HDAC2, HDAC3, HDAC4, HDAC5, HDAC6, and the like), histone acetylases, nucleic acid, histones, and the like. These HDAC7-interacting proteins form the basis of an additional aspect of the invention directed to the investigation, diagnosis and treatment of diseases associated with histone acetylation or deacetylation. In particular, the present invention provides isolated nucleic acids encoding these HDAC7-interacting proteins, their functional domains, or subsequences useful as probes or primers. These nucleic acids may be incorporated into a variety of recombinant DNA constructs, including vectors encoding fusion proteins and vectors for the transfection or transformation of cell lines and the production of animal models.

Thus, the present invention also provides transformed cell lines and transgenic animals bearing these nucleic acids which encode at least a functional domain of a HDAC7 or HDAC7-interacting protein. Using the cell lines and animal models of the invention, one is enabled to produce substantially pure peptides or proteins corresponding to these HDAC7 and HDAC7-interacting proteins, their functional domains, or at least their antigenic determinants. In addition, using these recombinantly produced proteins, or naturally produced but substantially purified HDAC7-interacting peptides, one is enabled to produce antibodies to these HDAC7-interacting proteins which will have utility in the assays described herein.

In accordance with another embodiment of the present invention, there are provided assays for compounds which modulate the interaction between HDAC7 and HDAC7-interacting proteins. In preferred embodiments, these assays are performed in a yeast two-hybrid system in which the interacting domains of a HDAC7 and a HDAC7-interacting protein are expressed in the hybrid fusion proteins and candidate compounds are tested for their ability to modulate this interaction. In other embodiments, the ability of a compound to modulate these interactions may be tested using the transformed cell lines and transgenic animals of the invention or by in vitro means (e.g., competitive binding assays). Candidate compounds that have been shown to modulate these interactions may be produced in pharmaceutically useful quantities, be tested in the animal models provided herein, and/or be tested in human clinical trials for their ability to provide therapeutic benefits.

In another embodiment of the present invention, screens are provided for diagnosing mutations in HDAC7-interacting proteins which may be causative of transcriptional diseases, such as neoplasias, related disorders, and the like. In addition, pharmaceutical compositions are provided, and methods of their use, for the treatment of such diseases and related disorders. These pharmaceuticals include compounds identified by the methods of the present invention which modulate the interactions between HDAC7 and the HDAC7-interacting proteins. Such pharmaceuticals also include peptide fragments of the interacting domains of both HDAC7 and the HDAC7-interacting proteins, as well as small molecule mimetics of these domains. These and other embodiments relating to the newly disclosed HDAC7-interacting proteins will be readily apparent from the following disclosure.

In accordance with another aspect of the invention, the proteins of the invention can be used as starting points for rational drug design to provide ligands, therapeutic drugs or other types of small chemical molecules. Alternatively, small molecules or other compounds identified by the above-described screening assays may serve as "lead compounds" in rational drug design.

The above disclosure generally describes the present invention. A more complete understanding can be obtained by reference to the following specific examples which are provided herein for purposes of illustration only and are not intended to limit the scope of the invention.

Without further elaboration, it is believed that one skilled in the art can, using the preceding description, utilize the present invention to its fullest extent. The following examples are intended to illustrate but not to limit the invention in any anner, shape, or form, either explicitly or implicitly. While they are typical of those that might be used, other procedures, methodologies, or techniques known to those skilled in the art may alternatively be used.

EXAMPLES

The transcriptional corepressor SMRT functions by mediating the repressive effect of transcription factors involved in diverse signaling pathways. The mechanism by which SMRT represses basal transcription has been proposed to involve the indirect recruitment of histone deacetylase HDAC1 via the adaptor mSin3A. In contrast to this model, a two-hybrid screen with SMRT interacting proteins resulted in the isolation of the recently described HDAC5 and a new family member termed HDAC7. Molecular and biochemical results indicate that this interaction is direct and in vivo evidence colocalize SMRT, mHDAC5, and mHDAC7 to a distinct nuclear compartment. Surprisingly, HDAC7 can interact with mSin3A in yeast and in mammalian cells, suggesting association of multiple repression complexes. Taken together, these results provide the first evidence that SMRT mediated repression is promoted by class I and class II histone deacetylases and that SMRT can recruit class II histone deacetylases in a mSin3A independent fashion. The findings described here indicate that two or more classes of histone deacetylases can collectively contribute to SMRT/N-CoR action and that at least some deacetylases may directly associate with SMRT/N-CoR in a mSin3A independent fashion.

Example 1

SMRT Interacts With Class II Deacetylases in Yeast

In order to determine if SMRT repression may be mediated through interaction with factors other than mSin3A, a yeast two-hybrid screen was conducted using SMRT repression domains III and IV (previously designated as SRD I and SRD II) as bait. Yeast two-hybrid screen and assays were carried out using standard lithium acetate method. Mouse embryonic 17 days yeast two hybrid library (Stratagene) and pGBT9-hSMRT (1060–1831) were co-transformed into yeast strain Y190. After three days, two isolated colonies were picked, resuspended in water, and 103 cells were dropped on both -Trp-Leu and -Trp-Leu-His+40 mM 3-AT plates. Approximately $5 \times 10^6$ yeast transformants were screened and selected on yeast minimal medium -Leu-Trp-His plates containing 40 mM 3-aminotriazole (Sigma). After 7 days, colonies were picked and confirmed by β-galactosidase assays. Plasmids were recovered from yeast and retransformed into yeast along with the bait construct. Positive clones were then subjected for sequencing.

This screen led to the isolation of several interacting clones whose products encode members of the newly described class II family of mammalian deacetylases. The majority of clones identified express the carboxyl-terminal histone deacetylase domain of the recently identified HDAC5 (Grozinger et al., 1999; Verdel and Khochbin, 1999). Two of the clones, however, encode a novel class II histone deacetylase, which is termed HDAC7.

Example 2

SMRT and HDAC Interaction

A yeast β-galactosidase liquid assay was carried out to evaluate the interaction between SMRT and mHDAC5 and 7. The plasmids pCMX, pCMX-GAL4 DBD and pMH100-TK-luc have been described (Nagy et al., 1997, supra). Standard PCR amplifications and subcloning techniques were employed to generate pCMX C-terminal HA epitope tagged and GAL4 fusion mHDAC5 and mHDAC7 constructs. All constructs were verified by double stranded sequencing to confirm identity and reading frame. The vector pCMX-SMRTα C-terminal Flag epitope tagged was constructed with cDNAs obtained from a previous screen (Ordentlich et al., 1999, supra) which describes the isolation and characterization of the SMRTα full-length cDNA. Clone 32A, which encodes the C-terminal deacetylase domain of HDAC5 was first tested. In the presence of the bait construct GAL DBD-SMRT (RD III+IV), increased reporter activity is observed, indicating an association between SMRT and mHDAC5 (FIG. 1A). Interestingly, deletion of the C-terminal sequence to the HDAC5 deacetylase domain dramatically decreased reporter activity (FIG. 1B). Similar results were obtained when clone 23C, which encodes C-terminal sequence of mHDAC7, was used.

Examination of these interacting clones indicated that the minimal SMRT interacting domain encompasses the beginning of the histone deacetylase domain. Since the catalytic cores of the histone deacetylases are similar to each other, experiments were conducted to determine whether SMRT could also interact with other histone deacetylases such as HDAC1, HDAC3, and mHDAC6 (also designated mHDA2;

(Verdel and Khochbin, 1999, supra)). A series of AD-HDAC constructs were generated for interaction assays in yeast. Transformants harboring both plasmids were picked and patched onto nutrient selection plates. Only cells that contain plasmids carrying an interacting partner are able to activate reporter gene HIS3 and therefore are viable in the selection plate -Trp-Leu-His+40 mM 3-AT. In contrast to mHDAC5 and 7, the deacetylase domains of HDAC1, HDAC3, and mHDAC6 do not interact with SMRT (SMRT RDIII and IV) in a yeast two-hybrid assay. The bait construct pGBT9-SMRT (RD III+IV) was cotransformed with GAL AD-fusion to varies HDAC constructs into yeast strain Y190. After three days, two isolated colonies were picked, resuspended in water, and 103 cells were dropped on both -Trp-Leu and -Trp-Leu-His+40 mM 3-AT plates. Pictures were taken after three days. These results indicate that association with HDAC5 and 7 is specific and not an intrinsic property of the deacetylase domain.

Example 3

Isolation of mHDAC7, a New Member of the Novel Histone Deacetylases

To obtain the full-length cDNAs of mHDAC5 and mHDAC7, a mouse brain library was probed with DNA fragments from the yeast library clones. Probes used in the isolation of full-length mouse HDAC5 and 7 cDNAs were isolated (EcoRI/BglII) from the pGAD4-2.1 vector containing the partial cDNAs obtained from the yeast two-hybrid screen. Accordingly, a mouse brain cDNA lamba ZAP II library (Stratagene) was screened at low stringency. After two successive rounds the full-length cDNA sequences for mHDAC5 and 7 were isolated and sequenced on both strands by standard methods. Overlapping clones were obtained for both mouse mHDAC5 and mHDAC7. The full-length mHDAC5 contains an additional 123 amino acid in its N-terminal compared to previous reported mHDA1. In addition, the previously reported mHDA1 encodes a 991 amino acid polypeptide which is 131 amino acids shorter than its human homologue HDAC5 and therefore is likely an incomplete cDNA or a spliced variant (Verdel and Khochbin, 1999). Sequence comparison of human and mouse HDAC5 reveals an overall 95% amino acid sequence identity.

Figure 2C:
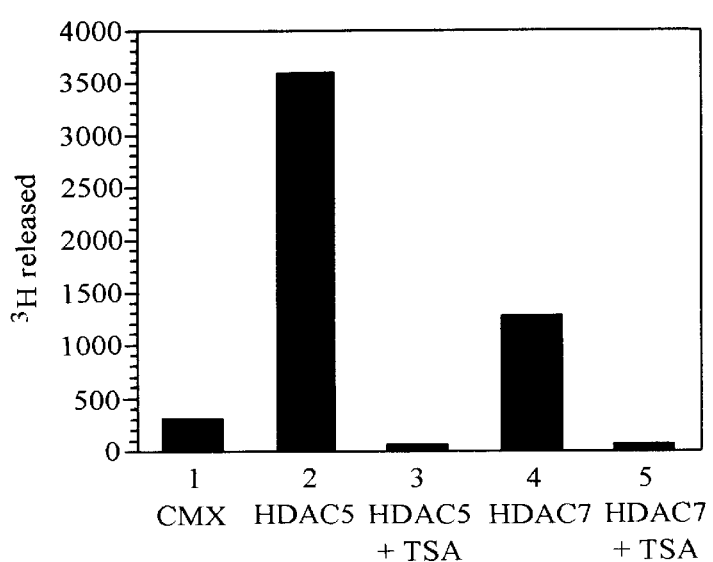
FIG. 2C graphs the association of mHDAC5 and 7 with histone deacetylase activity. Whole cell extracts prepared from cells expressing vector alone, mHDAC5 (bars 2 and 3) and mHDAC7 (bars 4 and 5) were immunoprecipitated with anti-HA antibodies conjugated agarose beads. Immunoprecipitates were resuspended in deacetylase assay buffer for histone deacetylase assays in the presence (bars 3 and 5) or absence (bars 2 and 4) of 100 nM Trichostatin A.

The longest reading frame for mHDAC7 encodes a protein of 938 amino acids with an expected molecular weight of 101 kDa. Sequence alignment of HDAC4, mHDAC5, and mHDAC7 performed according to Jotun Hein method using DNA STAR program reveals that these three proteins share extensive sequence homology (FIG. 2A). Overall mHDAC7 shares 46% and 42% amino acid sequence identity to HDAC4 and HDAC5, respectively (FIG. 2B). The C-terminal region, which includes a well conserved histone deacetylase domain (overall 80% amino acid sequence identity) and the SMRT interacting domain in both HDAC5 and 7 are mapped to this region. Unlike HDAC4, 5, and 7, HDAC6 contains two histone deacetylase domains of decreased conservation followed by a unique sequence including 3 copies of CXXC zinc finger motif. A northern probed with mHDAC7 revealed high levels of expression of a 4.2-Kb transcript in heart and lung, with low levels in skeletal muscle (FIG. 2C). The probe generated with a 1768 bp cDNA EcoRI/HindIII fragment from pCMX-HDAC7 was used to hybridize a mouse poly A$^+$ RNA blot (Clonetech #7762-1) using standard hybridization and washing protocols.

Figure 2D:
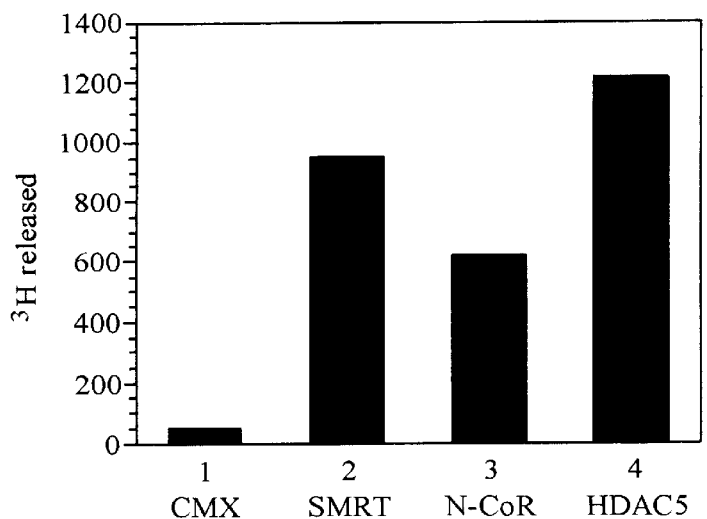
FIG. 2D graphs the association of SMRT and N-CoR with histone deacetylase activity.

Previously HDAC5 has been shown to possess histone deacetylase activity. To test whether mHDAC7 can also function as a histone deacetylase, Histone deacetylase assays were performed according to Heinzel et. al., (Heinzel et al., 1997). HA epitope-tagged HDAC5 and HDAC7 were expressed in 293 cells, immunoprecipitated, and assayed for their enzymatic activity in vitro. The immunoprecipitates were incubated for 2 hours at 37° C. with 60000 cpm of purified $^3$H-acetate labeled histones. Reactions were stopped by addition of acetic acid/HCL to a final concentration of 0.12 N/0.72 N and extracted with 2 volumes of ethyl acetate. Samples were centrifuged and the amount of released $^3$H-acetate supernatant was measured by scintillation counting (FIG. 2D). Each reaction represents approximately ⅓ of a transfected 10 cm plate of cells. Histone deacetylase activity was carried out in the absence and presence of 100 nM of TSABoth mHDAC5 and mHDAC7 exhibit HDAC activity (lanes 2 and 4) which is completely abolished by treatment with 100 nM of TSA (lanes 3 and 5). Similarly using Flag epitope-tagged SMRT and N-CoR, it was also demonstrated that both proteins can immunoprecipitate HDAC activity (FIG. 2E).

Example 4 mHDAC5 and mHDAC7 Repress Basal Transcription

Transient transfection experiments were conducted to examine the ability of mHDAC5 and mHDAC7 to repress basal transcription in mammalian cells. Monkey CV-1 cells were grown in DMEM supplemented with 10% FBS, 50 units/ml of penicillin G, and 50 µg/ml of streptomycin sulfate at 37° C. in 7% CO$_2$. CV-1 cells (60–70% confluence, 48 well plate) were cotransfected with 16.6 ng to 66.6 ng of pCMXGAL4 and pCMXGAL4-HDAC constructs, 100 ng of pMH100-TK-Luc, and 100 ng of pCMX-LacZ in 200 µl of DMEM containing 10% FBS by the N-[1-(2,3-dioleoyloxy)propyl]-N,N,N-trimethylammonium methylsulfate (DOTAP)-mediated procedure. Full-length mHDAC5, mHDAC7, and HDAC1 were fused to the GAL4 DNA binding domain (DBD) 1–147. The amount of DNA in each transfection was kept constant by addition of pCMX. After 24 hr, the medium was replaced and cells were harvested and assayed for luciferase activity 36–48 hrs after transfection. The luciferase activity was normalized by the level of β-galactosidase activity. Each transfection was performed in triplicate and repeated at least three times.

Figure 3A:
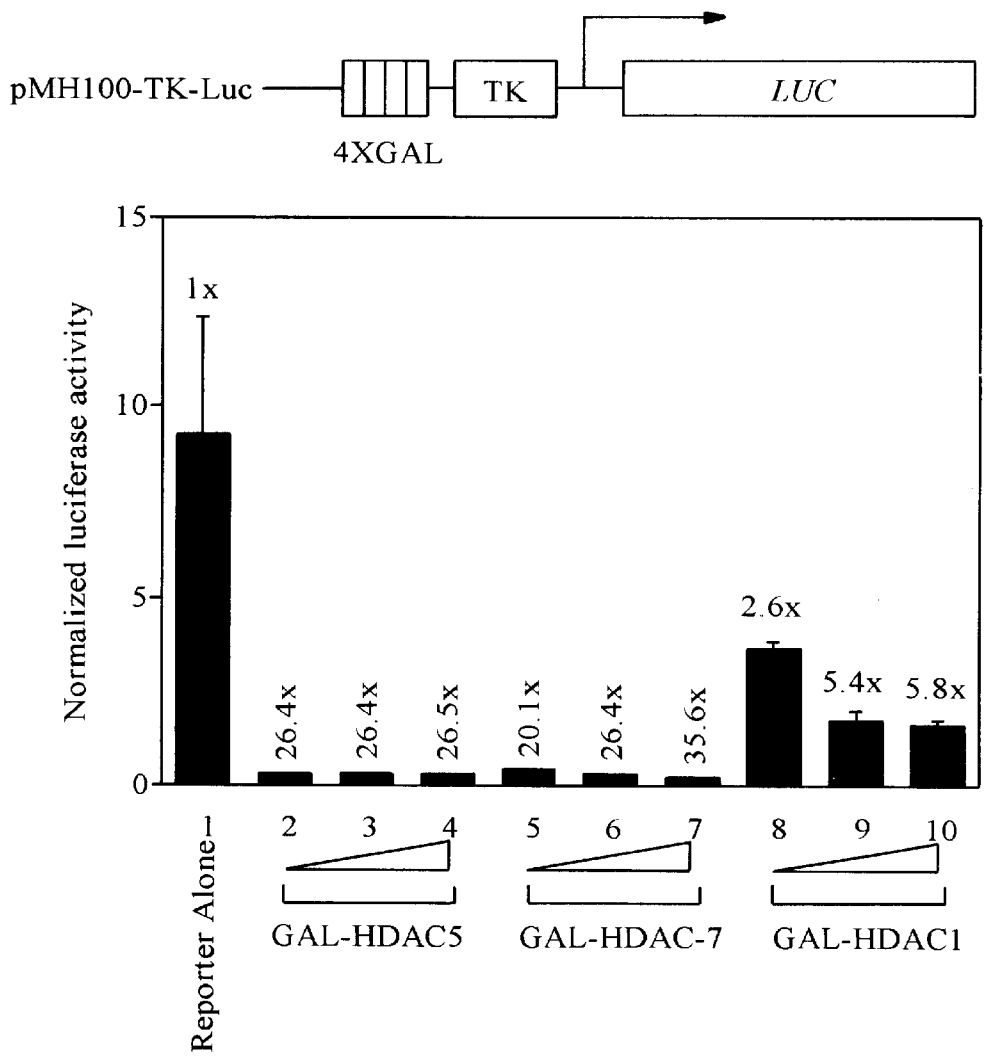
FIG. 3A is a graph depicting HDAC5 and HDAC7 repression of basal transcription in transient transfection assays. CV-1 cells were transfected with reporter constructs pCMX-β-GAL and pMH100-TK-Luc as well as increasing amounts of plasmids expressing GAL-mHADC5 (bars 2–4), GAL-mHADC7 (bars 5–7), and GAL-HDAC1 (bars 8–10). Bar 1 is a control. Fold of repression activity is shown at the top of each bar.

Repression activity was determined by transiently transfecting increasing amounts of the GAL-fusion vectors along with reporter constructs (FIG. 3A). Fold repression was determined relative to the basal transcription activity of the reporter in the presence of the GAL4 DBD. Both mHDAC5 and mHDAC7 gave over twenty-five fold repression activity at each concentration tested, and were substantially more active than GAL4 DBD-HDAC1.

Figure 3B:
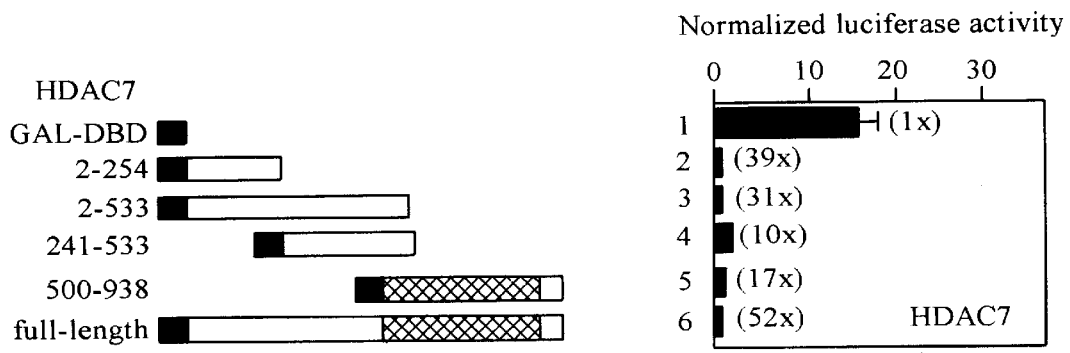
FIG. 3B illustrates the three repression domains of mHDAC7. The GAL DBD1-147 was fused to the N-terminal of a series of truncation constructs of mHDAC7, and 0.1 μg of the fusion construct was tested in transient transfection assays for repression activity. Fold repression is shown on the top of each bar. Fold repression was determined relative to the basal transcription activity of the reporter in the presence of GAL4 DBD.
Figure 3C:
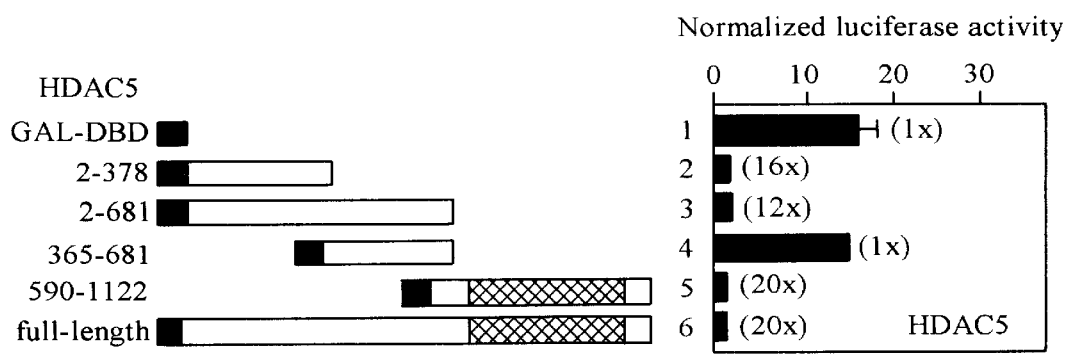
FIG. 3C depicts the two repression domains of mHDAC5. The assays were carried out the same as described for FIG. 3B except that the GAL DBD-mHDAC5 constructs were used.

To further define repression domains of mHDAC5 and 7, a set of deletion and truncation constructs of mHDAC5 and 7 fused to GAL4 DBD was made for repression assays. This led to the identification of two autonomous repression domains in mHDAC5 and three repression domains in mHDAC7. In addition to the deacetylase domain at the carboxyl terminus of mHDAC7, two additional repression domains corresponding to amino acids 2–254 (R1) and 241–533 (R2) were identified (FIG. 3B). Similarly, HDAC5 contains a single repression domain (R1) corresponding to amino acids 2–378 (FIG. 3C). While the repression activities of the deacetylase domain are expected, the potent activities of these additional regions suggest potential new autonomous repressor functions.

Example 5

SMRT Interacts With mHDAC5 and mnHDAC7 In Vitro and In Vivo

Figure 4:
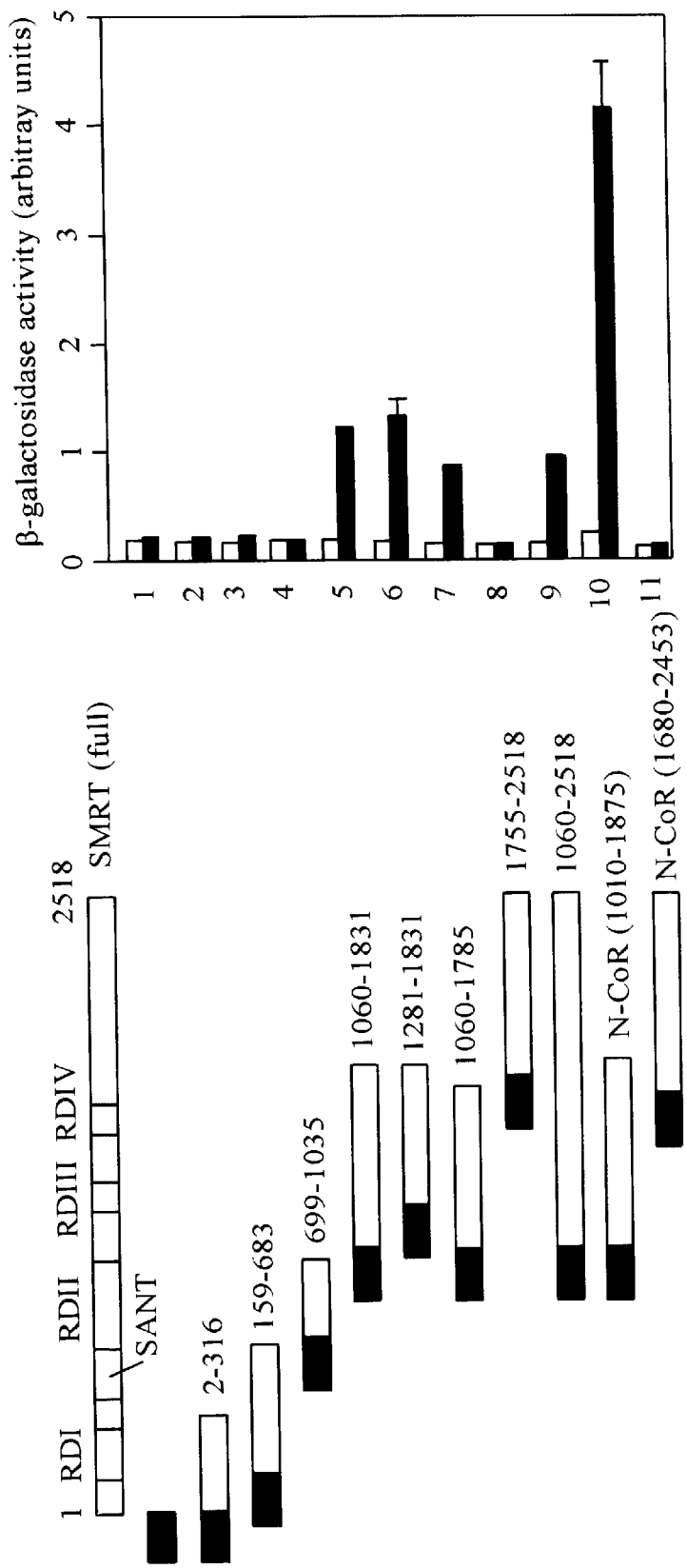
FIG. 4 provides a summary of yeast two hybrid assays. SMRT contains four repression domains denoted as RD I, II, III, and IV. RD III and IV were renamed from SRD I and II, respectively. Note that the HDAC5 interacting domain was mapped to amino acids 1281–1785. Quantitation of the yeast two-hybrid assays is indicated following each construct shown.

To map the region in SMRT that interacts with HDAC5, a series of SMRT deletion and truncation constructs were generated and tested in a yeast two-hybrid assay. As described earlier, an association between SMRT RD III and IV with C-terminal sequence of HDAC5 was observed. In contrast, GAL4 DBD fusions of repression domains I or II (RD I or II), however, failed to show any HDAC5 association. In summary, the minimal HDAC5 interacting domain was mapped to amino acid 1281–1785 (FIG. 4). HDAC7 also interacts with SMRT in the RD III/IV region (data not shown). In a similar experiment, when a GAL DBD-N-CoR (1016–1875) which spans RD III and IV was used, a high reporter activity was observed, suggesting that association between SMRT and mHDAC5/7 is also conserved in N-CoR. Whether SMRT sequences other than RD III and IV can interact with HDAC1 and mHDAC6 in yeast was also investigated. Interestingly, no interaction was found (data not shown). A set of deletion and truncation constructs of HDAC5 was also generated to map SMRT interaction domains. Our results indicate that SMRT interacting domain resides at the conserved C-terminal region, which includes the deacetylase domain of both HDAC5 and 7.

A GST pull down assay was employed to determine whether mHDAC5 interacts with SMRT in vitro. Glutathione S-transferase fusion protein with the mHDAC5 carboxyl-terminal containing histone deacetylase domain was expressed in E. coli DH5αa strain and affinity purified by glutathione Sepharose 4B beads. In vitro pull down assays were carried out by incubating GST fusion proteins with nuclear extracts prepared from 293 cells expressing SMRT-Flag protein in G buffer (Kao et al., 1998) for 1 hr at 4° C. on a nutator. After extensive washes protein sample buffer was added to retained fractions, boiled, and separated on 7.5% SDS-PAGE. Western blot analyses probed with anti-HA antibodies were carried out using standard protocols to detect whether SMRT is present in the pull-down fraction. This data reveals that GST-mHDAC5 can directly bind SMRT or interacts with SMRT associated proteins.

To confirm the interaction between SMRT and mHDAC5 and mHDAC7 in mammalian cells, coimmunoprecipitation experiments were conducted. SMRT interacts with HDAC5 and HDAC7 in mammalian cells. Anti-Flag antibodies were incubated with whole cell extracts prepared from cells expressing mHDAC5-HA, mHDAC7-HA, mHDAC5-HA and SMRT-Flag, and mHDAC7-HA and SMRT-Flag. Immunoprecipitates were separated onto SDS-PAGE and Western analysis was carried out using anti-HA antibodies as a probe. The expression level of mHDAC5-HA and mHDAC7-HA is equivalent in all extracts as determined by Western blots. For immunoprecipitations, 293 cells were transfected with 15 μmg of the appropriate plasmid expressing mHDAC5/7-HA or both SMRT-Flag and mHDAC5/7-HA using Targefect F1 (Targeting Systems, San Diego). The expression level of mHDACs is equivalent in all samples. Cells were harvested 48 hours later by lysing in 50 mM Tris pH 8.0, 150 mM NaCl, 10% Glycerol, 0.5% Triton, ImM PMSF and protease inhibitors. Cells were lysed for 15 minutes at 4°, scraped and centrifuged 15 minutes at 13 k rpm. Supernatant was kept as whole cell extract. After preclearing by incubation with A/G agarose (Santa Cruz), immunoprecipitations were carried out using either HA-agarose (Santa Cruz) or M2-agarose (Sigma) and proceeded for 2 hours at 4°. Beads were washed 3–4 times in lysis buffer without Triton, for histone deacetylase assays, and PBS with 0.1% NP40 for co-immunoprecipitations. For co-immunoprecipitations, samples were boiled in SDS loading buffer, separated on SDS-PAGE gels, transferred to nitrocellulose membrane and probed with the appropriate antibodies. In supporting previous results, mHDAC5-HA and mHDAC7-HA were precipitated by anti-Flag antibodies only in the presence of SMRT-Flag.

Example 6

SMRT, mHDAC5, and mHDAC7 Co-localize in Subnuclear Regions

To examine the subcellular localization of the HDAC5 and 7 proteins in CV-1 cells, cells transfected with plasmid expressing YFP-mHDAC5 or 7 were visualized by fluorescence microscopy and the resulting images were deconvolved using Deltavision2 software. CV-1 cells were plated into 2-well chamber slides (Nunc) and transfected using Targefect F1 (Targeting Systems). After 48 hours, cells were washed in PBS, fixed in 3.7% paraformaldehyde and permeabilized with 1% Triton X-100. For immunostaining, fixed cells were incubated with antibodies against SMRT (MAI-843, Affinity Bioreagents) and CBP (06-297, Upstate Biotechnology) for 1 hour, washed, and incubated with secondary antibody (Cy3 or Cy5) for 1 hour. Cells were washed and mounted using Permount. DAPI was included in the final wash to visualize nuclei. Images were visualized using an Olympus 1×70 inverted system microscope equipped with CCD. The resulting images were deconvolved using Deltavision2 software.

Interestingly, both mHDAC5 (see below) and mHDAC7 were found predominantly in the nucleus with distinct subnuclear dot-like structures. Furthermore, YFP-mHDAC5 and 7 staining did not overlap with DAPI staining. To address the possibility that mHDAC5 and mHDAC7 co-localize, plasmids expressing YFP-mHDAC5 and CFP-mHDAC7 were generated and cotransfected into CV-1 cells. It was found that mHDAC5 and mHDAC7 co-localized in the same subnuclear compartment. Whether mHDAC5 could co-localize with endogenous SMRT was also examined. CV-1 cells transfected with YFP-mHDAC5 were subjected to indirect immunofluorescence with anti-SMRT and anti-CREB-binding protein (CBP) antibodies, which was used as a control. While mHDAC5 and SMRT were found to completely overlap in subnuclear structures, mHDAC5 and CBP did not co-localize, strengthening the notion that mHDAC5 and SMRT associates in vivo.

Example 7 mHDAC7 Interacts With mSin3A in Mammalian Cells and in Yeast

Figure 5A:
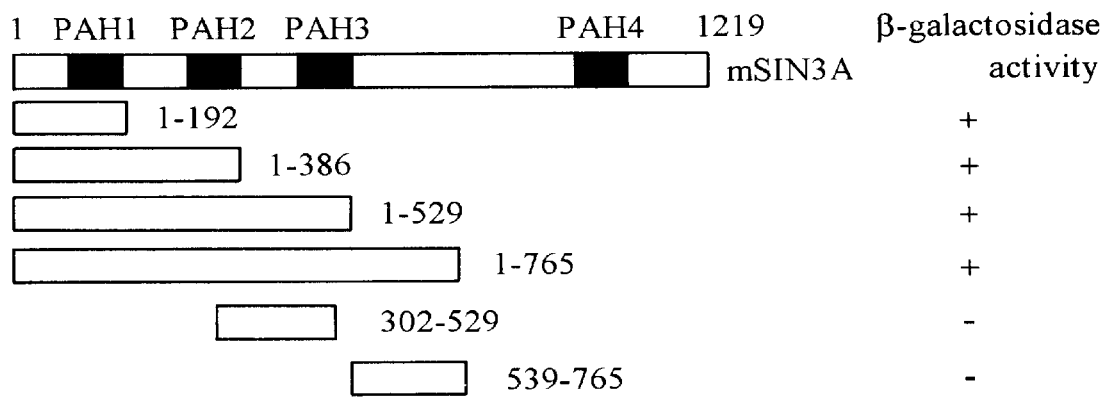
FIG. 5A illustrates mHDAC7 interaction with PAH1 of mSin3A in yeast. Plasmids pGBT9-HDAC7 (500–938) and pACTII-mSin3A were co-transformed into yeast Y190 strain and β-galactosidase lifting assays were performed.
Figure 5B:
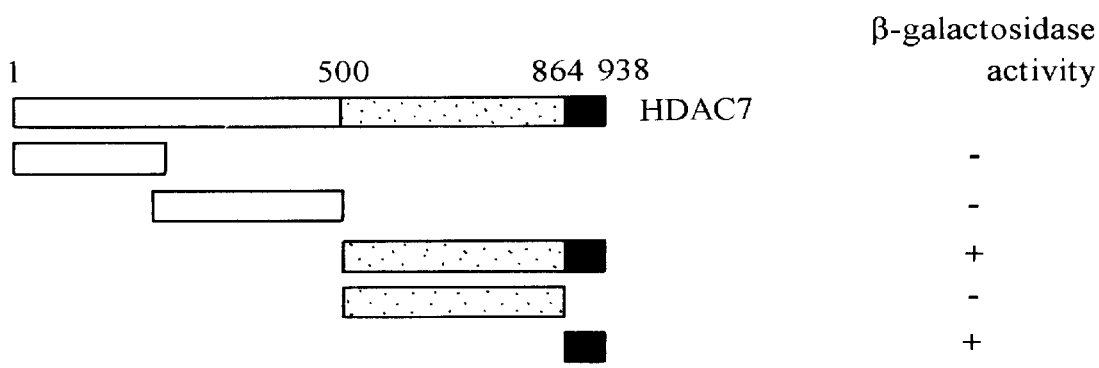
FIG. 5B shows that the C-terminal region (amino acids 864–938) of HDAC7 is required for mSin3A interaction. Plasmids pGBT9-HDAC and pACTII-mSin3A (1–386) were co-transformed into yeast strain Y190 in this experiment.
Figure 6C:
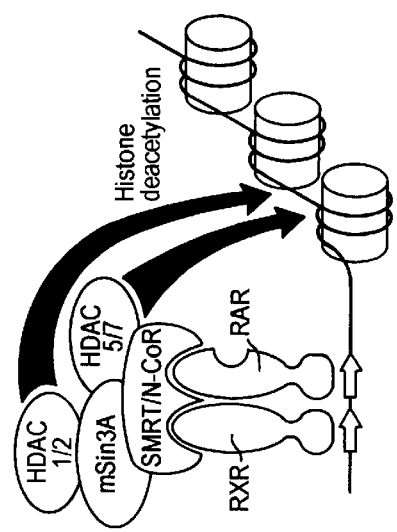
FIG. 6 depicts models of SMRT repression of transcription by recruiting both class I and class II histone deacetylases. Repression by sequence-specific transcription factor such as nuclear receptor heterodimer of retinoid X receptor (RXR) and retinoid acid receptor (RAR) is mediated by SMRT corepressor complex that represses transcription by recruiting both class I and class II histone deacetylases. Models for mechanism of SMRT repression include: (A) SMRT recruits class I deacetylase HDAC1/HDAC2 through direct interaction with mSin3A; (B) SMRT represses transcription by direct interaction with class II deacetylases HDAC5 and HDAC7 (and possibly HDAC4); which also bind to mSin3A through a region different from where HDAC1 binds mSin3A; and (C) SMRT recruits both class I and class II histone deacetylases and mSin3A.
Figure 6B:
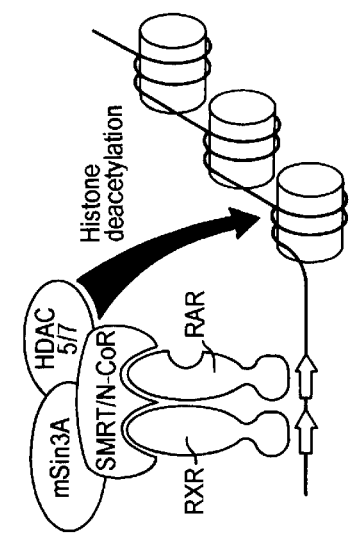
Figure 6A:
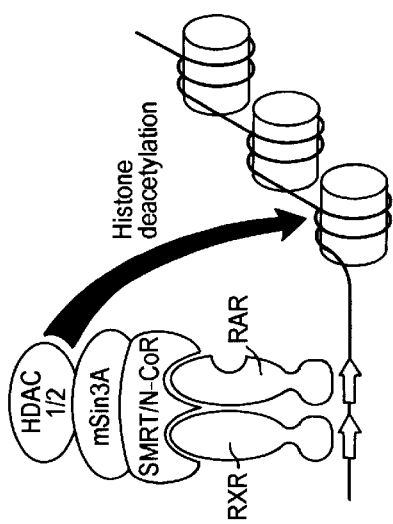

Given that SMRT interacts with mSin3A and that mSin3A interacts with HDAC1, the possibility that mHDAC7 might also interact with mSin3A was investigated. To address this, a coimmunoprecipitation experiment was employed. 293 cells were transfected with a plasmid expressing mHDAC7-HA. Lysates were prepared from cells with or without mHDAC7-HA expression and incubated with anti-HA antibodies conjugated agarose beads. mHDAC7 complexes with mSin3A in yeast and in mammalian cells. The cells were lysed in NET-N buffer. Immunoprecipitates were probed with anti-HA, anti-SMRT, and anti-mSin3A antibodies. SMRT and mSin3A were specifically immunoprecipitated in the presence of mHDAC7-HA, indicating that HDAC7, SMRT, and mSin3A can exist as part of a ternary complex. Whole cell extracts prepared from 293 cells with or without mHDAC7-HA expression were incubated with anti-HA antibodies conjugated with agarose beads. Immunoprecipitates were subjected to Western blot analysis and probed with anti-HA antibodies, anti-mSin3A antibodies, and anti-SMRT antibodies. To test whether mHDAC7 physically interacts with mSin3A, a yeast two-hybrid assay was conducted with a series of GAL DBD-mHDAC7 and AD-mSin3A constructs. It was found that mSin3A interacts with mHDAC7 through N-terminal 192 amino acids containing the first amphipathic helix (PAH1), which apparently differs from the interaction between HDAC1 and mSin3A (FIG. 5A). Furthermore, mSin3A interaction domain was mapped to the C-terminal 74 amino acids of HDAC7, which does not include the deacetylase domain (FIG. 5B).

While the invention has been described in detail with reference to certain preferred embodiments thereof, it will be understood that modifications and variations are within the spirit and scope of that which is described and claimed.

That which is claimed:

1. An isolated polynucleotide, wherein said isolated polynucleotide is selected from the group consisting of:
   (i) a polynucleotide encoding a histone deacetylase (HDAC), wherein said histone deacetylase comprises an mSin3A interacting domain comprising an amino acid sequence as set forth in amino acids 864–938 of SEQ ID NO:2, or conservative substitutions thereof,
   (ii) a fragment of at least 50 contiguous nucleotides of the polynucleotide of (i), and
   (iii) a full complement of (i) or (ii);
      wherein said histone deacetylase interacts in an mSin3A independent manner with Silencing Mediator for Retinoic and Thyroid receptors (SMRT), nuclear receptor co-repressor (N-CoR), or an isoform or peptide portion of SMRT or N-CoR.

2. The isolated polynucleotide according to claim 1, wherein said HDAC further comprises a SMRT interacting domain.

3. The isolated polynucleotide according to claim 2, wherein said SMRT interacting domain is coextensive with a deacetlyation domain of said HDAC.

4. The isolated polynucleotide of claim 1, wherein said HDAC interacts with SMRT Repression Domains (RD) III and IV.

5. The isolated polynucleotide according to claim 1, wherein said HDAC interacts with mSin3A.

6. The isolated polynucleotide according to claim 1, wherein said HDAC is capable of forming a ternary complex with SMRT/N-CoR and mSin3A.

7. The isolated polynucleotide according to claim 1, wherein said mSin3A interacting domain interacts with the 192 N-terminal amino acid domain of mSin3A.

8. The isolated polynucleotide according to claim 1, wherein said HDAC further comprises a repression domain.

9. The isolated polynucleotide according to claim 8, wherein said repression domain has the amino acid sequence set forth in amino acids 2–254 of SEQ ID NO:2, or conservative substitutions thereof.

10. The isolated polynucleotide according to claim 8, wherein said repression domain comprises the amino acid sequence set forth in amino acids 241–533 of SEQ ID NO:2, or conservative substitutions thereof.

11. The isolated polynucleotide according to claim 1, wherein said HDAC further comprises a deacetylase domain.

12. The isolated polynucleotide according to claim 11, wherein said deacetylase domain comprises the amino acid sequence as set forth in amino acids 500–938 of SEQ ID NO:2, or conservative substitutions thereof.

13. The isolated polynucleotide according to claim 1, wherein said polynucleotide encodes an immunogenic fragment of said HDAC.

14. An isolated polynucleotide that hybridizes under stringent conditions with a histone deacetylase encoding polynucleotide having the nucleotide sequence of SEQ ID NO: 1, wherein said stringent conditions comprise hybridization conditions of 40–65° C. and 0.1×SSC; wherein said histone deacetylase interacts in an mSin3A independent manner with Silencing Mediator for Retinoic and Thyroid receptors (SMRT), nuclear receptor co-repressor (N-CoR), or an isoform or peptide portion of SMRT or N-CoR.

15. The isolated polynucleotide according to claim 1, wherein said polynucleotide comprises the nucleic acid sequence set forth in SEQ ID NO:1.

16. The isolated polynucleotide according to claim 1, wherein said polynucleotide encodes the amino acid sequence of SEQ ID NO:2, or conservative substitutions thereof.

17. The isolated polynucleotide according to claim 1, wherein said HDAC comprises the amino acid sequence of SEQ ID NO:2, or conservative substitutions thereof.

18. A vector comprising a polynucleotide according to claim 1.

19. A host cell containing the vector according to claim 18.

20. A host cell containing a polynucleotide according to claim 1.

21. A cell line containing a polynucleotide according to claim 1.

22. A cell line containing the vector according to claim 21.

23. An isolated polynucleotide, wherein said isolated polynucleotide is selected from the group consisting of:
   (i) a polynucleotide encoding a histone deacetylase (HDAC), wherein said histone deacetylase comprises a repression domain comprising an amino acid sequence set forth in amino acids 2–254 of SEQ ID NO:2, or conservative substitutions thereof, (ii) a fragment of at least 50 contiguous nucleotides of the polynucleotide of (i), and (iii) a full complement of (i) or (ii);

wherein said histone deacetylase interacts in an mSin3A independent manner with Silencing Mediator for Retinoic and Thyroid receptors (SMRT), nuclear receptor co-repressor (N-CoR), or an isoform or peptide portion of SMRT or N-CoR.

24. An isolated polynucleotide, wherein said isolated polynucleotide is selected the group consisting of:

(i) a polynucleotide encoding a histone deacetylase (HDAC), wherein said histone deacetylase comprises a repression domain comprising an amino acid sequence set forth in amino acids 241–533 of SEQ ID NO:2, or conservative substitutions thereof, (ii) a fragment of at least 50 contiguous nucleotides of the polynucleotide of (i), and (iii) a fill complement of (i) or (ii);

wherein said histone deacetylase interacts in an mSin3A independent manner with Silencing Mediator for Retinoic and Thyroid receptors (SMRT), nuclear receptor co-repressor (N-CoR), or an isoform or peptide portion of SMRT or N-CoR.

25. An isolated polynucleotide, wherein said isolated polynucleotide is selected from the group consisting of:

(i) a polynucleotide encoding a histone deacetylase (HDAC), wherein said histone deacetylase comprises a deacetylase domain comprising an amino acid sequence set forth in amino acids 506–938 of SEQ ID NO:2, or conservative substitutions thereof, (ii) a fragment of at least 50 contiguous nucleotides of the polynucleotide of (i), and (iii) a full complement of (i) or (ii);

wherein said histone deacetylase interacts in an mSin3A independent manner with Silencing Mediator for Retinoic and Thyroid receptors (SMRT), nuclear receptor co-repressor (N-CoR), or an isoform or peptide portion of SMRT or N-CoR.

* * * * *

UNITED STATES PATENT AND TRADEMARK OFFICE
CERTIFICATE OF CORRECTION

PATENT NO. : 6,673,587 B1
DATED : January 6, 2004
INVENTOR(S) : Evans, Ronald M. et al.

It is certified that error appears in the above-identified patent and that said Letters Patent is hereby corrected as shown below:

Title page,
Item [54], Title, before "HISTONE" insert -- NOVEL --

Column 49,
Line 28, change "pucleotide" to -- nucleotide --

Column 51,
Line 13, after "selected" insert -- from --
Line 21, change the word "fill" to -- full --

Signed and Sealed this

Fourteenth Day of September, 2004

JON W. DUDAS
*Director of the United States Patent and Trademark Office*

SEQUENCE LISTING

<160> NUMBER OF SEQ ID NOS: 4

<210> SEQ ID NO 1
<211> LENGTH: 2871
<212> TYPE: DNA
<213> ORGANISM: Mus sp.

<400> SEQUENCE: 1

| | | | | | |
|---|---|---|---|---|---|
| atgcacagcc | ccggcgcggg | ctgccctgcc | ctccagccag | acacaccagg | ctctcagccc | 60 |
| caacccatgg | acctgcgggt | gggccagcgg | cccacggtgg | agccccacc | agagcctgcg | 120 |
| ctgctgaccc | tgcaacaccc | ccaacgcctg | caccgccatc | tcttcctggc | aggcttacac | 180 |
| cagcaacagc | gctcagccga | gcccatgagg | ctctccatgg | acccaccaat | gccggagctg | 240 |
| caggggggac | agcaggagca | agaacttcgg | caacttctca | ataaagacaa | gagcaagcga | 300 |
| agtgccgtag | ccagcagtgt | ggtcaagcag | aagctggctg | aagtgatcct | gaagaaacag | 360 |
| caggcagccc | ttgagagaac | agtccatccc | agcagcccca | gtattcccta | cagaactctt | 420 |
| gagcccttgg | acacagaggg | tgctgcccgc | tccgtgctta | gcagcttcct | gcctcctgtt | 480 |
| cccagcctgc | ccactgaacc | cccggaacac | tttcccttgc | gtaaaacagt | gtctgaaccc | 540 |
| aacctgaagt | tgcgctacaa | acccaagaaa | tccctggaga | gacgcaagaa | tcccctgctc | 600 |
| aggaaggaga | gtgccccgcc | cagccttcgg | aggaggcctg | ccgagaccct | tggagattcc | 660 |
| tcccccagta | gtagcagcac | acccgcgtca | gggtgcagct | ccctaatga | cagcgagcat | 720 |
| ggccctaacc | ctgccctagg | ctcagaggct | gatggtgacc | gcaggaccca | ttcaacttta | 780 |
| ggccctcggg | gtcctgtact | ggggaacccc | catgctcccc | tcttcctgca | ccacggtctg | 840 |
| gagccagagg | ctgggggcac | cttaccctct | cgcctgcaac | ccattctcct | gctggacccc | 900 |
| tcagtctctc | atgccccact | gtggactgtg | cctggccttg | ggcccttgcc | cttccacttt | 960 |
| gcccagccct | tactgaccac | cgagcggctc | tctgggtcag | gcctccatcg | accacttaac | 1020 |
| cggacccgct | cagagcccct | gcccccagc | gccacagcct | cccctctgct | ggcccccctg | 1080 |
| cagccccgcc | aggatcggct | caaacctcac | gtccagctga | tcaagccagc | catctcccct | 1140 |
| ccccagaggc | ctgccaagcc | cagtgagaag | ccccgactgc | gacagatacc | ctcggctgag | 1200 |
| gacctagaga | cagatggtgg | gggagtggga | cctatggcga | atgatggcct | ggaacatagg | 1260 |
| gagtcaggcc | gtgggcctcc | tgagggcaga | ggctccattt | ctctgcagca | gcaccaacag | 1320 |
| gtgccaccct | gggagcagca | gcatctagcc | gggcggctct | ctcagggaag | cccggggac | 1380 |
| tccgtgctga | tacctctggc | ccaggttgga | caccggcccc | tgtccagaac | ccagtcttcc | 1440 |
| ccagcagcac | ctgtttccat | gttgagccca | gagcccacct | gtcagaccca | agtcctcaac | 1500 |
| agctcagaga | cacctgctac | agggctggtc | tatgactcgg | tgatgctgaa | acaccaatgt | 1560 |
| tcctgtggag | acaacagcaa | gcatcccgag | catgcaggcc | gcatccagag | catctggtcc | 1620 |

-continued

```
cggctgcagg aacgggtct ccgcagccag tgtgagtgtc tccgaggccg aaaggcttcc    1680
ctagaggagc tgcagtcagt ccactctgaa cggcacgtgc tcctttacgg cacgaaccca    1740
ctcagccgcc tcaaactgga taacgggaag cttacaggac tcctggcaca gcggacgttt    1800
gtgatgctac cctgtggcgg ggttggggtc gatactgaca ccatctggaa cgagctgcat    1860
tcctccaatg cagcccgctg ggctgcgggc agtgtcaccg accttgcctt caaagtagct    1920
tcccgagagc tgaagaatgg ctttgctgtg gtgcgacccc cgggacacca tgcagatcat    1980
tctacagcca tgggcttctg cttcttcaac tccgtgccca tcgcctgccg acagctacag    2040
caacacggca agccagcaa gatcctcatt gttgactggg atgttcacca tggcaacggc    2100
acacagcaga ctttctacca ggaccccagt gtgctctaca tttcccttca tcgccatgac    2160
gacggcaact tcttcccagg cagtgggggcc gtggatgagg tgggaactgc cagtggcgag    2220
ggcttcaatg tcaacgtggc ttgggctggg ggcttggatc cacccatggg ggatcctgag    2280
tacctggctg ctttcaggat agtggtgatg cccattgccc gagagtttgc tccagacctg    2340
gtcctggtgt ctgctgggtt tgatgctgcg gagggtcacc cagccccgct gggtggctac    2400
catgtttctg ccaaatgttt tgggtacatg acgcagcagt tgatgaactt ggcaggaggc    2460
gccgtggtgt tggccttaga gggtggacat gacctcacgg ccatctgtga tgcctcggag    2520
gcctgtgtag ctgctcttct gggcaacaag gtggaccccc tttcagaaga aagctggaaa    2580
cagaaaccca acctcagtgc catccgctcg ctggaagctg tggtcagggt gcacaggaaa    2640
tactggggct gcatgcagcg cttggcctcc tgtccagact cctggctacc cagagtgccg    2700
ggagctgatg cagaagtgga agccgtgacc gcgctggcat ccctttctgt gggcatcctg    2760
gctgaagaca ggccctcgga gcggctggtg aagaggaag aacccatgaa cctctagggt    2820
ttcagaacag atcgcgcttc aaatgtggct ctcctcgtct ctgatgtcag c             2871
```

<210> SEQ ID NO 2
<211> LENGTH: 938
<212> TYPE: PRT
<213> ORGANISM: Mus sp.

<400> SEQUENCE: 2

```
Met His Ser Pro Gly Ala Gly Cys Pro Ala Leu Gln Pro Asp Thr Pro
 1               5                  10                  15

Gly Ser Gln Pro Gln Pro Met Asp Leu Arg Val Gly Gln Arg Pro Thr
            20                  25                  30

Val Glu Pro Pro Glu Pro Ala Leu Leu Thr Leu Gln His Pro Gln
        35                  40                  45

Arg Leu His Arg His Leu Phe Leu Ala Gly Leu His Gln Gln Gln Arg
    50                  55                  60

Ser Ala Glu Pro Met Arg Leu Ser Met Asp Pro Pro Met Pro Glu Leu
65                  70                  75                  80

Gln Gly Gly Gln Gln Glu Gln Glu Leu Arg Gln Leu Leu Asn Lys Asp
                85                  90                  95

Lys Ser Lys Arg Ser Ala Val Ala Ser Ser Val Lys Gln Lys Leu
            100                 105                 110

Ala Glu Val Ile Leu Lys Lys Gln Gln Ala Ala Leu Glu Arg Thr Val
        115                 120                 125

His Pro Ser Ser Pro Ser Ile Pro Tyr Arg Thr Leu Glu Pro Leu Asp
    130                 135                 140

Thr Glu Gly Ala Ala Arg Ser Val Leu Ser Ser Phe Leu Pro Pro Val
```

-continued

```
              145                 150                 155                 160
        Pro Ser Leu Pro Thr Glu Pro Glu His Phe Pro Leu Arg Lys Thr
                        165                 170                 175

Val Ser Glu Pro Asn Leu Lys Leu Arg Tyr Lys Pro Lys Lys Ser Leu
                        180                 185                 190

Glu Arg Arg Lys Asn Pro Leu Leu Arg Lys Glu Ser Ala Pro Pro Ser
                        195                 200                 205

Leu Arg Arg Arg Pro Ala Glu Thr Leu Gly Asp Ser Pro Ser Ser
                210                 215                 220

Ser Ser Thr Pro Ala Ser Gly Cys Ser Ser Pro Asn Asp Ser Glu His
        225                 230                 235                 240

Gly Pro Asn Pro Ala Leu Gly Ser Glu Ala Asp Gly Asp Arg Arg Thr
                        245                 250                 255

His Ser Thr Leu Gly Pro Arg Gly Pro Val Leu Gly Asn Pro His Ala
                        260                 265                 270

Pro Leu Phe Leu His His Gly Leu Glu Pro Glu Ala Gly Gly Thr Leu
                        275                 280                 285

Pro Ser Arg Leu Gln Pro Ile Leu Leu Leu Asp Pro Ser Val Ser His
                        290                 295                 300

Ala Pro Leu Trp Thr Val Pro Gly Leu Gly Pro Leu Pro Phe His Phe
        305                 310                 315                 320

Ala Gln Pro Leu Leu Thr Thr Glu Arg Leu Ser Gly Ser Gly Leu His
                        325                 330                 335

Arg Pro Leu Asn Arg Thr Arg Ser Glu Pro Leu Pro Pro Ser Ala Thr
                        340                 345                 350

Ala Ser Pro Leu Leu Ala Pro Leu Gln Pro Arg Gln Asp Arg Leu Lys
                        355                 360                 365

Pro His Val Gln Leu Ile Lys Pro Ala Ile Ser Pro Pro Gln Arg Pro
                        370                 375                 380

Ala Lys Pro Ser Glu Lys Pro Arg Leu Arg Gln Ile Pro Ser Ala Glu
        385                 390                 395                 400

Asp Leu Glu Thr Asp Gly Gly Gly Val Gly Pro Met Ala Asn Asp Gly
                        405                 410                 415

Leu Glu His Arg Glu Ser Gly Arg Gly Pro Pro Glu Gly Arg Gly Ser
                        420                 425                 430

Ile Ser Leu Gln Gln His Gln Gln Val Pro Pro Trp Glu Gln Gln His
                        435                 440                 445

Leu Ala Gly Arg Leu Ser Gln Gly Ser Pro Gly Asp Ser Val Leu Ile
                450                 455                 460

Pro Leu Ala Gln Val Gly His Arg Pro Leu Ser Arg Thr Gln Ser Ser
        465                 470                 475                 480

Pro Ala Ala Pro Val Ser Met Leu Ser Pro Glu Pro Thr Cys Gln Thr
                        485                 490                 495

Gln Val Leu Asn Ser Ser Glu Thr Pro Ala Thr Gly Leu Val Tyr Asp
                        500                 505                 510

Ser Val Met Leu Lys His Gln Cys Ser Cys Gly Asp Asn Ser Lys His
                        515                 520                 525

Pro Glu His Ala Gly Arg Ile Gln Ser Ile Trp Ser Arg Leu Gln Glu
                        530                 535                 540

Arg Gly Leu Arg Ser Gln Cys Glu Cys Leu Arg Gly Arg Lys Ala Ser
        545                 550                 555                 560

Leu Glu Glu Leu Gln Ser Val His Ser Glu Arg His Val Leu Leu Tyr
                        565                 570                 575
```

Gly Thr Asn Pro Leu Ser Arg Leu Lys Leu Asp Asn Gly Lys Leu Thr
            580                 585                 590
Gly Leu Leu Ala Gln Arg Thr Phe Val Met Leu Pro Cys Gly Gly Val
        595                 600                 605
Gly Val Asp Thr Asp Thr Ile Trp Asn Glu Leu His Ser Ser Asn Ala
    610                 615                 620
Ala Arg Trp Ala Ala Gly Ser Val Thr Asp Leu Ala Phe Lys Val Ala
625                 630                 635                 640
Ser Arg Glu Leu Lys Asn Gly Phe Ala Val Arg Pro Pro Gly His
                645                 650                 655
His Ala Asp His Ser Thr Ala Met Gly Phe Cys Phe Asn Ser Val
            660                 665                 670
Ala Ile Ala Cys Arg Gln Leu Gln Gln His Gly Lys Ala Ser Lys Ile
            675                 680                 685
Leu Ile Val Asp Trp Asp Val His His Gly Asn Gly Thr Gln Gln Thr
            690                 695                 700
Phe Tyr Gln Asp Pro Ser Val Leu Tyr Ile Ser Leu His Arg His Asp
705                 710                 715                 720
Asp Gly Asn Phe Phe Pro Gly Ser Gly Ala Val Asp Glu Val Gly Thr
                725                 730                 735
Ala Ser Gly Glu Gly Phe Asn Val Asn Val Ala Trp Ala Gly Gly Leu
            740                 745                 750
Asp Pro Pro Met Gly Asp Pro Glu Tyr Leu Ala Ala Phe Arg Ile Val
            755                 760                 765
Val Met Pro Ile Ala Arg Glu Phe Ala Pro Asp Leu Val Leu Val Ser
770                 775                 780
Ala Gly Phe Asp Ala Ala Glu Gly His Pro Ala Pro Leu Gly Gly Tyr
785                 790                 795                 800
His Val Ser Ala Lys Cys Phe Gly Tyr Met Thr Gln Gln Leu Met Asn
                805                 810                 815
Leu Ala Gly Gly Ala Val Val Leu Ala Leu Glu Gly Gly His Asp Leu
            820                 825                 830
Thr Ala Ile Cys Asp Ala Ser Glu Ala Cys Val Ala Ala Leu Leu Gly
            835                 840                 845
Asn Lys Val Asp Pro Leu Ser Glu Glu Ser Trp Lys Gln Lys Pro Asn
850                 855                 860
Leu Ser Ala Ile Arg Ser Leu Glu Ala Val Val Arg Val His Arg Lys
865                 870                 875                 880
Tyr Trp Gly Cys Met Gln Arg Leu Ala Ser Cys Pro Asp Ser Trp Leu
                885                 890                 895
Pro Arg Val Pro Gly Ala Asp Ala Glu Val Glu Ala Val Thr Ala Leu
            900                 905                 910
Ala Ser Leu Ser Val Gly Ile Leu Ala Glu Asp Arg Pro Ser Glu Arg
            915                 920                 925
Leu Val Glu Glu Glu Glu Pro Met Asn Leu
    930                 935

<210> SEQ ID NO 3
<211> LENGTH: 1084
<212> TYPE: PRT
<213> ORGANISM: Homo sapiens

<400> SEQUENCE: 3

Met Ser Ser Gln Ser His Pro Asp Gly Leu Ser Gly Arg Asp Gln Pro

-continued

```
  1               5                   10                  15
Val Glu Leu Leu Asn Pro Ala Arg Val Asn His Met Pro Ser Thr Val
                20                  25                  30
Asp Val Ala Thr Ala Leu Pro Leu Gln Val Ala Pro Ser Ala Val Pro
            35                  40                  45
Met Asp Leu Arg Leu Asp His Gln Phe Ser Leu Pro Val Ala Glu Pro
        50                  55                  60
Ala Leu Arg Glu Gln Gln Leu Gln Gln Glu Leu Leu Ala Leu Lys Gln
65                  70                  75                  80
Lys Gln Gln Ile Gln Arg Gln Ile Leu Ile Ala Glu Phe Gln Arg Gln
                85                  90                  95
His Glu Gln Leu Ser Arg Gln His Glu Ala Gln Leu His Glu His Ile
            100                 105                 110
Lys Gln Gln Gln Glu Met Leu Ala Met Lys His Gln Gln Glu Leu Leu
        115                 120                 125
Glu His Gln Arg Lys Leu Glu Arg His Arg Gln Glu Gln Glu Leu Glu
    130                 135                 140
Lys Gln His Arg Glu Gln Lys Leu Gln Gln Leu Lys Asn Lys Glu Lys
145                 150                 155                 160
Gly Lys Glu Ser Ala Val Ala Ser Thr Glu Val Lys Met Lys Leu Gln
                165                 170                 175
Glu Phe Val Leu Asn Lys Lys Ala Leu Ala His Arg Asn Leu Asn
            180                 185                 190
His Cys Ile Ser Ser Asp Pro Arg Tyr Trp Tyr Gly Lys Thr Gln His
        195                 200                 205
Ser Ser Leu Asp Gln Ser Ser Pro Pro Gln Ser Gly Val Ser Thr Ser
    210                 215                 220
Tyr Asn His Pro Val Leu Gly Met Tyr Asp Ala Lys Asp Asp Phe Pro
225                 230                 235                 240
Leu Arg Lys Thr Ala Ser Glu Pro Asn Leu Lys Leu Arg Ser Arg Leu
                245                 250                 255
Lys Gln Lys Val Ala Glu Arg Arg Ser Ser Pro Leu Leu Arg Arg Lys
            260                 265                 270
Asp Gly Pro Val Val Thr Ala Leu Lys Lys Arg Pro Leu Asp Val Thr
        275                 280                 285
Asp Ser Ala Cys Ser Ser Ala Pro Gly Ser Gly Pro Ser Ser Pro Asn
    290                 295                 300
Asn Ser Ser Gly Ser Val Ser Ala Glu Asn Gly Ile Ala Pro Ala Val
305                 310                 315                 320
Pro Ser Ile Pro Ala Glu Thr Ser Leu Ala His Arg Leu Val Ala Arg
                325                 330                 335
Glu Gly Ser Ala Ala Pro Leu Pro Leu Tyr Thr Ser Pro Ser Leu Pro
            340                 345                 350
Asn Ile Thr Leu Gly Leu Pro Ala Thr Gly Pro Ser Ala Gly Thr Ala
        355                 360                 365
Gly Gln Gln Asp Thr Glu Arg Leu Thr Leu Pro Ala Leu Gln Gln Arg
    370                 375                 380
Leu Ser Leu Phe Pro Gly Thr His Leu Thr Pro Tyr Leu Ser Thr Ser
385                 390                 395                 400
Pro Leu Glu Arg Asp Gly Gly Ala Ala His Ser Pro Leu Leu Gln His
                405                 410                 415
Met Val Leu Leu Glu Gln Pro Pro Ala Gln Ala Pro Leu Val Thr Gly
            420                 425                 430
```

```
Leu Gly Ala Leu Pro Leu His Ala Gln Ser Leu Val Gly Ala Asp Arg
        435                 440                 445

Val Ser Pro Ser Ile His Lys Leu Arg Gln His Arg Pro Leu Gly Arg
450                 455                 460

Thr Gln Ser Ala Pro Leu Pro Gln Asn Ala Gln Ala Leu Gln His Leu
465                 470                 475                 480

Val Ile Gln Gln Gln His Gln Gln Phe Leu Glu Lys His Lys Gln Gln
                485                 490                 495

Phe Gln Gln Gln Leu Gln Met Asn Lys Ile Ile Pro Lys Pro Ser
            500                 505                 510

Glu Pro Ala Arg Gln Pro Glu Ser His Pro Glu Glu Thr Glu Glu Glu
            515                 520                 525

Leu Arg Glu His Gln Ala Leu Leu Asp Glu Pro Tyr Leu Asp Arg Leu
        530                 535                 540

Pro Gly Gln Lys Glu Ala His Ala Gln Ala Gly Val Gln Val Lys Gln
545                 550                 555                 560

Glu Pro Ile Glu Ser Asp Glu Glu Ala Glu Pro Pro Arg Glu Val
                565                 570                 575

Glu Pro Gly Gln Arg Gln Pro Ser Glu Gln Glu Leu Leu Phe Arg Gln
            580                 585                 590

Gln Ala Leu Leu Leu Glu Gln Gln Arg Ile His Gln Leu Arg Asn Tyr
        595                 600                 605

Gln Ala Ser Met Glu Ala Ala Gly Ile Pro Val Ser Phe Gly Gly His
        610                 615                 620

Arg Pro Leu Ser Arg Ala Gln Ser Ser Pro Ala Ser Ala Thr Phe Pro
625                 630                 635                 640

Val Ser Val Gln Glu Pro Pro Thr Lys Pro Arg Phe Thr Thr Gly Leu
                645                 650                 655

Val Tyr Asp Thr Leu Met Leu Lys His Gln Cys Thr Cys Gly Ser Ser
            660                 665                 670

Ser Ser His Pro Glu His Ala Gly Arg Ile Gln Ser Ile Trp Ser Arg
        675                 680                 685

Leu Gln Glu Thr Gly Leu Arg Gly Lys Cys Glu Cys Ile Arg Gly Arg
        690                 695                 700

Lys Ala Thr Leu Glu Glu Leu Gln Thr Val His Ser Glu Ala His Thr
705                 710                 715                 720

Leu Leu Tyr Gly Thr Asn Pro Leu Asn Arg Gln Lys Leu Asp Ser Lys
                725                 730                 735

Lys Leu Leu Gly Ser Leu Ala Ser Val Phe Val Arg Leu Pro Cys Gly
            740                 745                 750

Gly Val Gly Val Asp Ser Asp Thr Ile Trp Asn Glu Val His Ser Ala
        755                 760                 765

Gly Ala Ala Arg Leu Ala Val Gly Cys Val Val Glu Leu Val Phe Lys
        770                 775                 780

Val Ala Thr Gly Glu Leu Lys Asn Gly Phe Ala Val Val Arg Pro Pro
785                 790                 795                 800

Gly His His Ala Glu Glu Ser Thr Pro Met Gly Phe Cys Tyr Phe Asn
                805                 810                 815

Ser Val Ala Val Ala Ala Lys Leu Leu Gln Gln Arg Leu Ser Val Ser
            820                 825                 830

Lys Ile Leu Ile Val Asp Trp Asp Val His His Gly Asn Gly Thr Gln
        835                 840                 845
```

```
Gln Ala Phe Tyr Ser Asp Pro Ser Val Leu Tyr Met Ser Leu His Arg
    850                 855                 860

Tyr Asp Asp Gly Asn Phe Phe Pro Gly Ser Gly Ala Pro Asp Glu Val
865                 870                 875                 880

Gly Thr Gly Pro Gly Val Gly Phe Asn Val Asn Met Ala Phe Thr Gly
                885                 890                 895

Gly Leu Asp Pro Pro Met Gly Asp Ala Glu Tyr Leu Ala Ala Phe Arg
            900                 905                 910

Thr Val Val Met Pro Ile Ala Ser Glu Phe Ala Pro Asp Val Val Leu
        915                 920                 925

Val Ser Ser Gly Phe Asp Ala Val Glu Gly His Pro Thr Pro Leu Gly
    930                 935                 940

Gly Tyr Asn Leu Ser Ala Arg Cys Phe Gly Tyr Leu Thr Lys Gln Leu
945                 950                 955                 960

Met Gly Leu Ala Gly Gly Arg Ile Val Leu Ala Leu Glu Gly Gly His
                965                 970                 975

Asp Leu Thr Ala Ile Cys Asp Ala Ser Glu Ala Cys Val Ser Ala Leu
            980                 985                 990

Leu Gly Asn Glu Leu Asp Pro Leu Pro Glu Lys Val Leu Gln Gln Arg
        995                 1000                1005

Pro Asn Ala Asn Ala Val Arg Ser Met Glu Lys Val Met Glu Ile His
    1010                1015                1020

Ser Lys Tyr Trp Arg Cys Leu Gln Arg Thr Thr Ser Thr Ala Gly Arg
1025                1030                1035                1040

Ser Leu Ile Glu Ala Gln Thr Cys Glu Asn Glu Glu Ala Glu Thr Val
                1045                1050                1055

Thr Ala Met Ala Ser Leu Ser Val Gly Val Lys Pro Ala Glu Lys Arg
            1060                1065                1070

Pro Asp Glu Glu Pro Met Glu Glu Glu Pro Pro Leu
        1075                1080

<210> SEQ ID NO 4
<211> LENGTH: 1114
<212> TYPE: PRT
<213> ORGANISM: Mus sp.

<400> SEQUENCE: 4

Met Asn Ser Pro Asn Glu Ser Ala Asp Gly Met Ser Gly Arg Glu Pro
1               5                   10                  15

Ser Leu Glu Ile Leu Pro Arg Thr Pro Leu His Ser Ile Pro Val Ala
            20                  25                  30

Val Glu Val Lys Pro Val Leu Pro Gly Ala Met Pro Ser Ser Met Gly
        35                  40                  45

Gly Gly Gly Gly Ser Pro Ser Pro Val Glu Leu Arg Gly Ala Leu
    50                  55                  60

Ala Gly Pro Met Asp Pro Ala Leu Arg Glu Gln Gln Leu Gln Gln Glu
65                  70                  75                  80

Leu Leu Val Leu Lys Gln Gln Gln Gln Lys Gln Leu Leu Phe
                85                  90                  95

Ala Glu Phe Gln Lys Gln His Asp His Leu Thr Arg Gln His Glu Val
                100                 105                 110

Gln Leu Gln Lys His Leu Lys Gln Gln Glu Met Leu Ala Ala Lys
            115                 120                 125

Arg Gln Gln Glu Leu Glu Gln Gln Arg Gln Arg Glu Gln Arg Gln
        130                 135                 140
```

-continued

```
Glu Glu Leu Glu Lys Gln Arg Leu Glu Gln Gln Leu Leu Ile Leu Arg
145                 150                 155                 160

Asn Lys Glu Lys Ser Lys Glu Ser Ala Ile Ala Ser Thr Glu Val Lys
                165                 170                 175

Leu Arg Leu Gln Glu Phe Leu Leu Ser Lys Ser Lys Glu Pro Thr Pro
            180                 185                 190

Gly Gly Leu Asn His Ser Leu Pro Gln His Pro Lys Cys Trp Gly Ala
        195                 200                 205

His His Ala Ser Leu Asp Gln Ser Ser Pro Pro Gln Ser Gly Pro Pro
    210                 215                 220

Gly Thr Pro Pro Ser Tyr Lys Leu Pro Leu Leu Gly Pro Tyr Asp Ser
225                 230                 235                 240

Arg Asp Asp Phe Pro Leu Arg Lys Thr Ala Ser Glu Pro Asn Leu Lys
                245                 250                 255

Val Arg Ser Arg Leu Lys Gln Lys Val Ala Glu Arg Arg Ser Ser Pro
            260                 265                 270

Leu Leu Arg Arg Lys Asp Gly Thr Val Ile Ser Thr Phe Lys Lys Arg
        275                 280                 285

Ala Val Glu Ile Thr Gly Thr Gly Pro Gly Val Ser Ser Val Cys Asn
    290                 295                 300

Ser Ala Pro Gly Ser Gly Pro Ser Ser Pro Asn Ser Ser His Ser Thr
305                 310                 315                 320

Ile Ala Glu Asn Gly Phe Thr Gly Ser Val Pro Asn Ile Pro Thr Glu
                325                 330                 335

Met Ile Pro Gln His Arg Ala Leu Pro Leu Asp Ser Ser Pro Asn Gln
            340                 345                 350

Phe Ser Leu Tyr Thr Ser Pro Ser Leu Pro Asn Ile Ser Leu Gly Leu
        355                 360                 365

Gln Ala Thr Val Thr Val Thr Asn Ser His Leu Thr Ala Ser Pro Lys
    370                 375                 380

Leu Ser Thr Gln Gln Glu Ala Glu Arg Gln Ala Leu Gln Ser Leu Arg
385                 390                 395                 400

Gln Gly Gly Thr Leu Thr Gly Lys Phe Met Ser Thr Ser Ser Ile Pro
                405                 410                 415

Gly Cys Leu Leu Gly Val Ala Leu Glu Gly Asp Thr Ser Pro His Gly
            420                 425                 430

His Ala Ser Leu Leu Gln His Val Cys Ser Trp Thr Gly Arg Gln Gln
        435                 440                 445

Ser Thr Leu Ile Ala Val Pro Leu His Gly Gln Ser Pro Leu Val Thr
    450                 455                 460

Gly Glu Arg Val Ala Thr Ser Met Arg Thr Val Gly Lys Leu Pro Arg
465                 470                 475                 480

His Arg Pro Leu Ser Arg Thr Gln Ser Ser Pro Leu Pro Gln Ser Pro
                485                 490                 495

Gln Ala Leu Gln Gln Leu Val Met Gln Gln His Gln Gln Phe Leu
            500                 505                 510

Glu Lys Gln Lys Gln Gln Gln Met Gln Leu Gly Lys Ile Leu Thr Lys
        515                 520                 525

Thr Gly Glu Leu Ser Arg Gln Pro Thr Thr His Pro Glu Glu Thr Glu
    530                 535                 540

Glu Glu Leu Thr Glu Gln Gln Glu Ala Leu Leu Gly Glu Gly Ala Leu
545                 550                 555                 560
```

-continued

```
Thr Ile Pro Arg Glu Gly Ser Thr Ser Glu Ser Thr Gln Glu Asp
            565                 570                 575
Leu Glu Glu Glu Glu Glu Glu Glu Glu Glu Glu Asp Cys Ile
        580                 585                 590
Gln Val Lys Asp Glu Asp Gly Glu Ser Gly Pro Asp Glu Gly Pro Asp
        595                 600                 605
Leu Glu Glu Ser Ser Ala Gly Tyr Lys Lys Leu Phe Ala Asp Ala Gln
    610                 615                 620
Gln Leu Gln Pro Leu Gln Val Tyr Gln Ala Pro Leu Ser Leu Ala Thr
625                 630                 635                 640
Val Pro His Gln Ala Leu Gly Arg Thr Gln Ser Ser Pro Ala Ala Pro
            645                 650                 655
Gly Ser Met Lys Ser Pro Thr Asp Gln Pro Thr Val Val Lys His Leu
            660                 665                 670
Phe Thr Thr Gly Val Val Tyr Asp Thr Phe Met Leu Lys His Gln Cys
            675                 680                 685
Met Cys Gly Asn Thr His Val His Pro Glu His Ala Gly Arg Ile Gln
        690                 695                 700
Ser Ile Trp Ser Arg Leu Gln Glu Thr Gly Leu Leu Gly Lys Cys Glu
705                 710                 715                 720
Arg Ile Arg Gly Arg Lys Ala Thr Leu Asp Glu Ile Gln Thr Val His
                725                 730                 735
Ser Glu Tyr His Thr Leu Leu Tyr Gly Thr Ser Pro Leu Asn Arg Gln
            740                 745                 750
Lys Leu Asp Ser Lys Lys Leu Leu Gly Pro Ile Ser Gln Lys Met Tyr
        755                 760                 765
Ala Met Leu Pro Cys Gly Gly Ile Gly Val Asp Ser Asp Thr Val Trp
        770                 775                 780
Asn Glu Met His Ser Ser Ala Val Arg Met Ala Val Gly Cys Leu
785                 790                 795                 800
Val Glu Leu Ala Phe Lys Val Ala Ala Gly Glu Leu Lys Asn Gly Phe
            805                 810                 815
Ala Ile Ile Arg Pro Pro Gly His His Ala Glu Glu Ser Thr Ala Met
            820                 825                 830
Gly Phe Cys Phe Phe Asn Ser Val Ala Ile Thr Ala Lys Leu Leu Gln
        835                 840                 845
Gln Lys Leu Ser Val Gly Lys Val Leu Ile Val Asp Trp Asp Ile His
        850                 855                 860
His Gly Asn Gly Thr Gln Gln Ala Phe Tyr Asn Asp Pro Ser Val Leu
865                 870                 875                 880
Tyr Ile Ser Leu His Arg Tyr Asp Asn Gly Asn Phe Phe Pro Gly Ser
            885                 890                 895
Gly Ala Pro Glu Glu Val Gly Gly Pro Gly Val Gly Tyr Asn Val
            900                 905                 910
Asn Val Ala Trp Thr Gly Gly Val Asp Pro Pro Ile Gly Asp Val Glu
            915                 920                 925
Tyr Leu Thr Ala Phe Arg Thr Val Met Pro Ile Ala Gln Glu Phe
        930                 935                 940
Ser Pro Asp Val Val Leu Val Ser Ala Gly Phe Asp Ala Val Glu Gly
945                 950                 955                 960
His Leu Ser Pro Leu Gly Gly Tyr Ser Val Thr Ala Arg Cys Phe Gly
            965                 970                 975
His Leu Thr Arg Gln Leu Met Thr Leu Ala Gly Gly Arg Val Val Leu
```

-continued

```
                       980                985                990
Ala Leu Glu Gly Gly His Asp Leu Thr Ala Ile Cys Asp Ala Ser Glu
            995               1000              1005

Ala Cys Val Ser Ala Leu Leu Ser Val Glu Leu Gln Pro Leu Asp Glu
   1010              1015              1020

Ala Val Leu Gln Gln Lys Pro Ser Val Asn Ala Val Ala Thr Leu Glu
1025              1030              1035              1040

Lys Val Ile Glu Ile Gln Ser Lys His Trp Ser Cys Val Gln Arg Phe
                 1045              1050              1055

Ala Ala Gly Leu Gly Cys Ser Leu Arg Glu Ala Gln Thr Gly Glu Lys
            1060              1065              1070

Glu Glu Ala Glu Thr Val Ser Ala Met Ala Leu Leu Ser Val Gly Ala
        1075              1080              1085

Glu Gln Ala Gln Ala Val Ala Thr Gln Glu His Ser Pro Arg Pro Ala
   1090              1095              1100

Glu Glu Pro Met Glu Gln Glu Pro Ala Leu
1105              1110
```